US009493567B2

(12) United States Patent
Lieberburg

(10) Patent No.: US 9,493,567 B2
(45) Date of Patent: *Nov. 15, 2016

(54) METHODS OF TREATING INFLAMMATORY AND AUTOIMMUNE DISEASES WITH NATALIZUMAB

(75) Inventor: Ivan Lieberburg, Berkeley, CA (US)

(73) Assignee: Biogen Inc., Cambridge, MA (US)

( * ) Notice: Subject to any disclaimer, the term of this patent is extended or adjusted under 35 U.S.C. 154(b) by 5 days.

This patent is subject to a terminal disclaimer.

(21) Appl. No.: 12/757,305

(22) Filed: Apr. 9, 2010

(65) Prior Publication Data

US 2010/0196318 A1 Aug. 5, 2010

Related U.S. Application Data

(62) Division of application No. 11/711,628, filed on Feb. 28, 2007.

(60) Provisional application No. 60/776,931, filed on Feb. 28, 2006.

(51) Int. Cl.
| | | |
|---|---|---|
| *A61K 39/395* | (2006.01) | |
| *C07K 16/28* | (2006.01) | |
| *G01N 33/68* | (2006.01) | |
| *A61K 39/00* | (2006.01) | |

(52) U.S. Cl.
CPC ........ *C07K 16/2842* (2013.01); *C07K 16/2839* (2013.01); *G01N 33/6896* (2013.01); *A61K 2039/505* (2013.01); *C07K 2317/24* (2013.01); *G01N 2333/025* (2013.01); *G01N 2800/285* (2013.01)

(58) Field of Classification Search
None
See application file for complete search history.

(56) References Cited

U.S. PATENT DOCUMENTS

| | | | |
|---|---|---|---|
| 5,840,299 A * | 11/1998 | Bendig et al. ............. | 424/133.1 |
| 6,033,665 A | 3/2000 | Yednock | |
| 6,229,011 B1 | 5/2001 | Chen et al. | |
| 6,238,859 B1 * | 5/2001 | Luke et al. ................ | 435/5 |
| 6,388,084 B1 | 5/2002 | Kaplan et al. | |
| 6,551,593 B1 | 4/2003 | Ringler et al. | |
| 6,602,503 B1 | 8/2003 | Lobb et al. | |
| 6,605,602 B1 * | 8/2003 | Vats .............................. | 514/85 |
| 7,008,949 B2 | 3/2006 | Konradi et al. | |
| 7,026,328 B2 | 4/2006 | Konradi et al. | |
| 7,026,501 B2 | 4/2006 | Kawaguchi et al. | |
| 7,101,855 B2 | 9/2006 | Dressen et al. | |
| 2002/0197233 A1 | 12/2002 | Relton et al. | |
| 2003/0176498 A1 | 9/2003 | Kawaguchi et al. | |
| 2004/0009169 A1 | 1/2004 | Taylor et al. | |
| 2004/0138243 A1 | 7/2004 | Konradi et al. | |
| 2004/0142954 A1 | 7/2004 | Konradi et al. | |
| 2006/0009385 A1 | 1/2006 | Hoffman et al. | |
| 2006/0013799 A1 | 1/2006 | Konradi et al. | |
| 2007/0142416 A1 | 6/2007 | Semko et al. | |
| 2008/0058357 A1 | 3/2008 | Smith et al. | |
| 2009/0169477 A1 | 7/2009 | Panzara et al. | |
| 2009/0216107 A1 * | 8/2009 | Rubin et al. ................ | 600/410 |

FOREIGN PATENT DOCUMENTS

| | | |
|---|---|---|
| WO | WO 2006/112951 | 10/2006 |
| WO | WO 2007/041270 | 4/2007 |
| WO | WO 2007/100763 | 9/2007 |
| WO | WO 2007/100770 | 9/2007 |
| WO | WO 2007/101165 | 9/2007 |
| WO | WO 2007/103112 | 9/2007 |

OTHER PUBLICATIONS

Public Health Advisory—Suspended Marketing of Tysabri (Natalizumab), Feb. 28, 2005.*
Langer-Gould et al., N Eng J Med 353: 375-381, 2005.*
Kleinschmidt-DeMasters et al., N Eng J Med 353:369-374, 2005.*
Knowles et al., Clinical and Diagnostic Virology 4: 183-194, 1995.*
Kieseier et al., Seminars in Neurology 23: 133-146, 2003.*
Hohlfeld et al., Seminars in Neurology 23:121-131, 2003.*
Gorelik et al., Ann. Neurol 68: 295-303, 2010.*
Yousry et al., New England Journal of Medicine 354: 924-933 (2006): Evaluation of Patients Treated with Natalizumab for Progressive Multifocal Leukoencephalopathy.*
Abraham et al., "A Small-Molecule, Tight-binding Inhibitor of the Integrin a4β1 Blocks Antigen-induced Airway Responses and Inflammation in Experimental Asthma in Sheep," Am. J. Respir. Crit. Care Med., 162:603-611 (2000).
Agostini et al., "Genotype Profile of Human Polyomavirus JC Excreted in Urine of Immunocompetent Individuals," J. Clin. Microbiol. 34:159-164 (1996).
Albrecht et al., "Highly active antiretroviral therapy significantly improves the prognosis of patients with HIV-associated progressive multifocal leukoencephalopathy," AIDS, 12:1149-1154 (1998).
Baron et al., "Surface Expression of a4 Integrin by CD4 T Cells Is Required for Their Entry Into Brain Parenchyma," J. Exp. Med. 177:57-68 (1993).
Berger et al., "Predictive Factors for Prolonged Survival in Acquired Immunodeficiency Syndrome-Associated Progressive Multifocal Leukoencephalopathy," Ann. Neurol., 44:341-349 (1998).
Berger, Jr. et al.: "Progressive multifocal leukoencephalopathy and natalizumab—Unforseen consequences"; New England Journal of Medicine Jul. 28, 2005; vol. 353, No. 4, Jul. 28, 2005, pp. 414-416.

(Continued)

*Primary Examiner* — Phillip Gambel
(74) *Attorney, Agent, or Firm* — Nathan Edwards; Ginger R. Dreger; Arnold & Porter LLP

(57) ABSTRACT

Natalizumab is a safe and efficacious treatment for inflammatory and autoimmune diseases, such as multiple sclerosis, Crohn's Disease, and rheumatoid arthritis. Rare occurrences of progressive multifocal leucoencephalopathy during treatment suggest the possibility that it may be related to natalizumab treatment. Monitoring for JCV and informing caregivers and patients about the manifestations of progressive multifocal leucoencephalopathy can improve the safety of natalizumab therapy.

12 Claims, No Drawings

(56) References Cited

OTHER PUBLICATIONS

Brennan, D.C., et al.; "Incidence of BK with tracrolimus versus cyclosporine and impact of preemptive immunosuppression reduction"; American Journal of Transplantation Mar. 2005 DK; vol. 5, No. 3, Mar. 2005, pp. 582-594.
Brocke et al., "Antibodies to CD44 and Integrin a4, but not L-selection, Prevent Central Nervous System Inflammation and Experimental Encephalomyelitis by Blocking Secondary Leukocyte Recruitment," Proc. Natl. Acad. Sci. 96:6896-6901 (1999).
Brück et al., "Inflammatory Central Nervous System Demyelination: Correlation of Magnetic Resonance Imaging Findings with Lesion Pathology," Ann. Neurol., 42:783-793 (1997).
Clifford et al., "HAART Improves Prognosis in HIV-associated Progressive Multifocal Leokoencephalopathy," Neurology 52:623-625 (1999).
Collazos, "Opportunistic Infections of the CNS in Patients with AIDS," CNS Drugs 17:869-887 (2003).
Co-pending U.S. Appl. No. 11/711,874, filed Feb. 28, 2007.
Co-pending U.S. Appl. No. 11/713,000, filed Mar. 2, 2007.
Crowder et al., "Successful Outcome of Progressive Multifocal Leukoencephalopathy in a Renal Transplant Patient," American Journal of Transplantation, 5:1151-1158 (2005).
Demeter, "JC, BK, and Other Polyomaviruses; Progressive Multifocal Leukoencephalopathy," Mandell, Douglas and Bennett's Principles and Practice of Infectious Diseases, Mandell et al. Eds., 4th Ed., New York, NY: Churchill Livingstone; 1995:1400-1406.
Dörries et al., "Association of Human Polyomavirus JC with Peripheral Blood of Immunoimpaired and Healthy Individuals," Journal of NeuroVirology, 9(suppl. 1);81-87 (2003).
Dörries et al., "Infection of Human Polyomaviruses JC and BK in Peripheral Blood Leukocytes from Immunocompetent Individuals," Virology, 198:59-70 (1994).
Dubois et al., "Detection of JC Virus DNA in the Peripheral Blood Leukocytes of HIV-infected Patients," AIDS 10:353-358 (1996).
Dworkin, "A Review of Progressive Multifocal Leukoencephalopathy in Persons With and Without AIDS," Curr. Clin. Top. Infect. Dis. 22:181-195 (2002).
Engelhardt, et al. "Therapeutic targeting of a4-integrins in chronic inflammatory diseases: tipping the scales of risk towards benefit?" Eur. J. Immunol., 35:2268-2273 (2005).
Enns et al., "Safety, Tolerability and Immunogenicity of Natalizumab in a Phase III Study of Active Crohn's Disease Therapy," Gastroenterology 126 (4, Suppl. 2): pA462 Apr. 2004.
Ernst et al., "Progressive Multifocal Leukoencephalopathy and Human Immunodeficiency Virus-associated White Matter Lesions in AIDS: Magnetization Transfer MR Imaging," Radiology 210:539-543 (1999).
Ferrante et al., "Detection of JC Virus DNA in Cerebrospinal Fluid from Multiple Sclerosis Patients," Multiple Sclerosis, 4:49-54 (1998).
Geschwind et al., "The Relative Contributions of HAART and Alpha-interferon for Therapy of Progressive Multifocal Leukoencephalopathy in AIDS," J. Neurovirol. 7:353-357 (2001).
Gibson et al., "Detection of JC Virus DNA in the Cerebrospinal Fluid of Patients With Progressive Multifocal Leukoencephalopathy," J. Med. Virol. 39:278-281 (1993).
Henson et al., "Amplification of JC Virus DNA from Brain and Cerebrospinal Fluid of Patients with Progressive Multifocal Leukoencephalopathy," Neurology 41: 1967-1971 (1991).
Hijazi et al., "Pharmacokinetics, Safety, and Tolerability of R411, a Dual a4β1-a4β7 Integrin Antagonist After Oral Administration at Single and Multiple Once-Daily Ascending Doses in Healthy Volunteers," J. Clin. Pharmacol., 44:1368-1378 (2004).
Hochberg, "A Sharper Bonferroni Procedure for Multiple Tests of Significance," Biometrika 75:800-802 (1988).
Hoffmann et al., "Progressive Multifocal Leucoencephalopathy with Unusual Inflammatory Response During Antiretroviral Treatment," J. Neurol. Neurosurg. Psychiatry 74:1142-1144 (2003).
Hurley et al., "Identification of HIV-Associated Progressive Multifocal Leukoencephalopathy: Magnetic Resonance Imaging and Spectroscopy," J. Neuropsychiatry Clin. Neurosci. 15:1-6 (2003).

IFNB Multiple Sclerosis Study Group, "Interferon Beta-1b is Effective in Relapsing-Remitting Multiple Sclerosis. I. Clinical Results of a Multicenter, Randomized, Double-blind, Placebo-controlled Trial,".
International Search Report for PCT/US06/06723 (I.e., WO 2006/112951 A2) dated Sep. 18, 2006.
International Search Report from PCT/US2007/004923, dated Sep. 22, 2008.
International Search Report from PCT/US2007/004943, dated Oct. 3, 2008.
International Search Report from PCT/US2007/05265, dated Oct. 2, 2007.
Isaac et al., "Multiple Sclerosis: A Serial Study Using MRI in Relapsing Patients," Neurology 38:1511-1515 (1988).
Jacobs et al., "Intramuscular Interferon Beta-1a for Disease Progression in Relapsing Multiple Sclerosis," Annals of Neurology, 39:285-294 (1996).
Johnson et al., "Copolymer 1 Reduces Relapse Rate and Improves Disability in Relapsimg-Remitting Multiple Sclerosis: Results of a Phase III Multicenter, Double-blind, Placebo-controlled Trial," Neurology 45:1268-1276 (1995).
Kappos et al., "Predictive Value of Gadolinium-enhanced Magentic Resonance Imaging for Relapse Rate and Changes in Disability or Impairment in Multiple Sclerosis: A Meta-analaysis," Lancet, 353:964-969 (1999).
Kent et al., "A Monoclonal Antibody to a4 Integrin Suppresses and Reverses Active Experimental Allergic Encephalomyelitis," J. Neuroimmunol. 58:1-10 (1995).
Khoury et al., "Longitudinal MRI in Multiple Sclerosis: Correlation Between Disability and Lesion Burden," Neurology 44:2120-2124 (1994).
Kitamura et al., "High Incidence of Urinary JC Virus Excretion in Nonimmunosuppressed Older Patients," J. Infect. Dis. 161:1128-1133 (1990).
Kleinschmidt-DeMasters et al., "Progressive Multifocal Leukoencephalopathy Complicationg Treatment with Natalizumab and Interferon Beta-1a for Multiple Sclerosis," N. Engl. J. Med. 353:369-374 (2005).
Knowles et al., "Prevalence of Long-Term BK and JC Excretion in HIV-Infected Adults and Lack of Correlation With Serological Markers," J. Med. Virol. 59:474-479 (1999).
Knowles et al., "The JC Virus Antibody Response in Serum and Cerebrospinal Fluid in Progressive Multifocal Leucoencephalophy," Clinical and Diagnostic Virology, 4:183-194 (1995).
Koralnik, "New Insights Into Progressive Multifocal Leukoencephalopathy," Current Opinion in Neurology, 17:365-370 (2004).
Kozovska et al., "Interferon Beta Induces T-helper 2 Immune Deviation in MS," Neurology 53:1692-1697 (1999).
Langer-Gould et al., "Progressive Multifocal ALeukoencephalopathy in a Patient Treated with Natalizumab," N. Eng. J. Med. 353:375-381 (2005).
Mamidi et al., "Central Nervous System Infections in Individuals with HIV-I Infection," J. Neurovirol. 8:158-167 (2002).
McDonald et al., "Recommended Diagnostic Criteria for Multiple Sclerosis: Guidelines from the International Panel on the Diagnosis of Multiple Sclerosis," Ann. Neurol., 50:121-127 (2001).
McFarland et al., "The Role of MRI as a Surrogate Outcome Measure in Multiple Sclerosis," Multiple Sclerosis 8:40-51 (2002).
Miller et al., "A Controlled Trial of Natalizumab for Relapsing Multiple Sclerosis," N. Engl. J. Med. 348:15-23 (2003).
Molyneux et al., "Correlations between Monthly Enhanced MRI Lesion Rate and Changes in T2 Lesion Volume in Multiple Sclerosis," Ann. Neurol., 43:332-339 (1998).
Office Action dated Dec. 24, 2009, for U.S. Appl. No. 11/713,000.
Office Action dated Jul. 20, 2010 for U.S. Appl. No. 11/713,000.
Office Action dated Jan. 20, 2011, for U.S. Appl. No. 11/713,000.
Office Action dated Jul. 30, 2010, for U.S. Appl. No. 11/711,874.
Office Action dated Nov. 27, 2009, for U.S. Appl. No. 11/711,874.
Olsen et al., "White Matter Disease in AIDS: Findings at MR Imaging," Radiology 169:445-448 (1988).
Padgett et al., "Virologic and Serologic Studies of Progressive Multifocal Leukoencephalopathy," Prog. Clin. Biol. Res. 105:107-117 (1983).
Pestalozza et al. Multiple Sclerosis. 2005. vol. 11, pp. 390-394.

(56) References Cited

OTHER PUBLICATIONS

Polman et al., "A Randomized, Placebo-Controlled Trail of Natalizumab for Relapsing Multiple Sclerosis," N. Engl. J. Med., 354(9):899-910 (2006).
Post et al., "Progressive Multifocal Leukoencephalopathy in AIDS: Are There Any MR Findings Useful to Patient Management and Predictive of Patient Survival?," Am. J. Neuroradiol. 20:1896-1906 (1999).
Prisms Study Group, "Randomised Double-blind Placebo-controlled Study of Interferon β-1a in Relapsing/Remitting Multiple Sclerosis," Lancet 352:1498-1504 (1998).
Przepiorka et al., "Successful Treatment of Progressive Multifocal Leukoencephalopathy with Low-Dose Interleukin-2," Bone Marrow Transplant, 20:983-987 (1997).
Redington et al., "Viral Infections of the Nervous System, 2002," Arch. Neurol: 59:712-718 (2002).
Rep et al., "Recombinant Interferon-β Blocks Proliferation but Enhances Interleukin-10 Secretion by Activated Human T-Cells," J. Neuroimmunol. 67:111-118 (1996).
Restriction Requirement dated Sep. 12, 2008 for U.S. Appl. No. 11/713,000.
Rudick et al., "Incidence and Significance of Neutralizing Antibodies to Interferon Beta-1a in Multiple Sclerosis," Neurology 50:1266-1272 (1998).
Rudick et al., "Natalizumab plus Interferon Beta-1a for Relapsing Multiple Sclerosis," N. Engl. J. Med., 354(9):911-923 (2006).
Salmaggi et al., "Reversal of CSF Positivity for JC Virus Genome by Cidofovir in a Patient with Systemic Lupus Erthematosus and Progressive Multifocal Leukoencephalopathy," Neurol. Sci. 22:17-20 (2001).
Schuurman et al., "Normal human immunoglobulin G4 is bispecific: it has two different antigen-combining sites," Immunology, 97:693-698 (1999).
Seth et al., "Advances in the Biology of JC Virus and Induction of Progressive Multifocal Leukoencephalopathy," J. Neurovirol. 9:236-246 (2003).
Shitrit et al.,"Progressive Multifocal Leukoencephalopathy in Transplant Recipients," Transpl. Int. 17:658-665 (2005).
Simon et al., "A Longitudinal Study of T1 Hypointense Lesions in Relapsing MS," Neurology 55:185-192 (2000).
Sundsfjord et al., "BK and JC Viruses in Human Immunodeficiency Virus Type 1-Infected Persons : Prevalence, Excretion, Viremia, and Viral Regulatory Regions," J. Infect. Dis. 169:485-490 (1994).
Tantisiriwat et al., "Progressive Multifocal Leukoencephalopathy in Patients with AIDS Receiving Highly Active Antiretroviral Therapy," Clin. Infect. Dis. 28:1152-1154 (1999).
Tenser, R.B. et al., "Natalizumab for Relapsing Multiple Sclerosis," New Engl. J. Med., 354(22): 2387-2389 (2006).
Thompson et al., "Major Differences in the Dynamics of Primary and Secondary Progressive Multiple Sclerosis," Ann. Neurol. 29:53-62 (1991).
Thompson et al., "Serial Gadolinium-Enhanced MRI in Relapsing/ Remitting Multiple Sclerosis of Varying Disease Duration," Neurology 42:60-63 (1992).
Tornatore et al., "Detection of JC Virus DNA in Peripheral Lymphocytes from Patients with and without Progressive Multifocal Leukoencephalopathy," Ann. Neurol., 31:454-462 (1992).
Vago et al., "JCV-DNA and BKV-DNA in the CNS Tissue and CSF of AIDS Patients and Normal Subjects. Study of 41 Cases and Review of the Literature," J. Acquir. Imm. Defic. Syndr. Hum. Retrovirol. 12:139-146 (1996).
Van Assche et al., "Physiological Basis for Novel Drug Therapies Used to Treat the Inflammatory Bowel Diseases: I. Immunology and therapeutic potential of antiadhesion molecule therapy in inflammatory bowel disease," Am. J. Physiol. Gastrointest. Liver Physiol., 288:G169-G174 (2005).
Van Assche et al., "Progressive Multifocal Leukoencephalophy after Natalizumab Therapy for Crohn's Disease," N. Eng. J. Med., 353:362-368 (2005).
von Andrian et al., "α4 Integrins as Therapeutic Targets in Autoimmune Disease" N. Engl. J. Med., 348(1):68-72.
Weber et al., "Progressive Multifocal Leukoencephalopathy Disgnosed by Amplification of JC Virus-specific DNA from Cerebrospinal Fluid," AIDS 8:49-57 (1994).
Weber et al., "Specific Diagnosis of Progressive Multifocal Leukoencephalopathy by Polymerase Chain Reaction," J. Infect. Dis. 169:1138-1141 (1994).
Whitaker et al., "Outcomes Assessment in Multiple Sclerosis Clinical Trials: a Critical Analysis," Multiple Sclerosis, 1:37-47 (1995).
Willoughby et al., "Serial Magnetic Resonance Scanning in Multiple Sclerosis: A Second Prospective Study in Relapsing Patients," Ann. Neurol., 25:43-49 (1989).
Yednock et al., "Prevention of Experimental Autoimmune Encephalomyelitis by Antibodies Against α4β1 Integrin," Nature 356:63-66 (1992).
Yousry et al. "Evaluation of Patients Treated with Natalizumab for Progressive Multifocal Leukoencephalopathy," N. Engl. J. Med., 354:924-33 (2006).
Zang et al., "Regulation of Chemokine Receptor CCR5 and Production of RANTES and MIP-1a by Interferon-β," J. Neuroimmunol. 112:174-180 (2001).
Weber et al., "Analysis of the Systemic and Intrathecal Humoral Immune Response in Progressive Multifocal Leukoencephalopathy", The Journal of Infectious Diseases 1997;176:250-254.
English Translation of excerpt from Japanese textbook entitled Immunology Illustrated, published on Feb. 10, 2000, 5th Edition, p. 102.
Steinman, L. "Blocking adhesion molecules as therapy for multiple sclerosis: natalizumab", Nature Reviews/Drug Discovery 4:510-518, 2005.
File History of U.S. Appl. No. 11/885,615, Amendment filed Nov. 22, 2010.
Engels et al., "Antibodies to JC and BK viruses among persons with non-Hodgkin lymphoma." Int. J. Cancer 2005, vol. 117, pp. 1013-1019.
Goelz et al., "Assay design and sample collection can affect anti-John Cunningham virus antibody detection." Ann. Neurol. 2011, vol. 69, pp. 429-431.
Gorelik et al., "Anti-JC virus antibodies: implications for PML risk stratification." Am. Neurol. Assoc. 2010, vol. 68, pp. 295-303.
Knowles et al., "Population-based study of antibody to the human polyomaviruses BKV and JCV and the Simian polyomavirus SV40." J. Med. Virol. 2003, vol. 71, pp. 115-123.
Ling et al., "The dynamics of herpesvirus and polyomavirus reactivation and shedding in healthy adults: a 14-month longitudinal study." J. Infect. Diseases 2003, vol. 187, pp. 1571-1580.
Rollison et al., "Prediagnostic circulating antibodies to JC and BK human polyomaviruses and risk of non-Hodgkin lymphoma." Cancer Epidemiol. Biomarkers Prev. 2006, vol. 15, No. 3, pp. 543-550.
Stolt et al., "Seroepidemiology of the human polyomaviruses." J. Gen. Virol. 2003, vol. 84, pp. 1499-1504.
Tur and Montalban, "Natalizumab: risk stratification of individual patients with Multiple Sclerosis." CNS Drugs 2014, vol. 28, pp. 641-648.
Chaudhuri, A. "Lessons for clinical trials from natalizumab in multiple sclerosis", BMJ 332:416-419, Feb. 18, 2006.
"Biogen IDEC and Elan Announce Voluntary Suspension of Tysabri®", Feb. 28, 2005, (http://www.biogenidec.com/press_archive.aspx?ID=6015).
Bloomgren, G. et al. "Risk of Natalizumab-Associated Progressive Multifocal Leukoencephalopathy", N Engl J Med. 2012; 366:1870-80.
Food and Drug Administration Label for Tysabri®—Revised May 24, 2013.

\* cited by examiner

METHODS OF TREATING INFLAMMATORY AND AUTOIMMUNE DISEASES WITH NATALIZUMAB

PRIORITY CLAIM

This application is a divisional application of U.S. patent application Ser. No. 11/711,628, filed Feb. 28, 2007, which claims priority to U.S. Provisional Application No. 60/776,931, filed Feb. 28, 2006, which are hereby incorporated herein for all purposes in their entireties.

TECHNICAL FIELD

The invention relates to methods of treating inflammatory and autoimmune diseases with a recombinant antibody. These methods improve the safety of treatment by informing and monitoring patients undergoing antibody treatment.

BACKGROUND ART

The migration of lymphocytes from the peripheral blood across the blood brain bather has been reported to initiate the development of several central nervous system (CNS) inflammatory diseases. Lymphocyte entry into the CNS is mediated by cellular adhesion molecules (O'Neill et al., *Immunology* 72:520-525 (1991); Raine et al., *Lab. Invest.* 63:476-489 (1990); Yednock et al., *Nature* 356:63-66 (1992); Baron et al., *J. Exp. Med.* 177:57-68 (1993); Steffen et al., *Am. J. Path.* 145:189-201 (1994); Christensen et al., *J. Immunol.* 154:5293-5301 (1995)).

Cellular adhesion molecules present on the cell surface mediate the direct binding of one cell to another (Long et al., *Exp. Hematol.* 20:288-301 (1992)). The integrin and immunoglobulin supergene families of adhesion molecules regulate lymphocyte traffic into the CNS (Hemler et al., *Annu. Rev. Immunol.* 8:365-400 (1990); Springer et al., *Cell* 76:301-314 (1994); Issekutz et al., *Curr. Opin. Immunol.* 4:287-293 (1992)). Adhesion molecules have been widely reported to mediate inflammatory and autoimmune diseases, for example, asthma, Alzheimer's disease, atherosclerosis, AIDS dementia, diabetes, inflammatory bowel disease, multiple sclerosis, rheumatoid arthritis, tissue transplantation rejection, and tumor metastasis.

Integrins are heterodimers of non-covalently linked α and β chains (Hemler et al., *Annu. Rev. Immunol.* 8:365-400 (1990)). The α4β1 (also called very late activation antigen-4 VLA-4) and α4β7 integrins are present on the surface of most types of white blood cells, where they mediate white cell binding to endothelial cells by interacting with their cognate receptors, vascular cell adhesion molecule-1 (VCAM-1) and mucosal addressin cellular adhesion molecule-1 (MAdCAM-1), on the endothelial cell surface. Integrins are believed to play an important role in immune cell adhesion to the endothelial cell layer on blood vessels, facilitating their subsequent migration into inflamed tissues. Several studies implicate VLA-4 and, in particular the α4 integrin subunit, in CNS inflammation (Yednock et al., *Nature* 356:63-66 (1992); Baron et al., *J. Exp. Med.* 177: 57-68 (1993); Steffen et al., *Am. J. Path.* 145:189-201 (1994); Christensen et al., *J. Immunol.* 154:5293-5301 (1995). It has also been reported that VCAM-1 expression is elevated in inflamed brain tissue relative to normal brain tissue (Cannella and Raine, *Ann. Neurol.* 37:424-435 (1995); Washington et al., *Ann. Neurol.* 35:89-97 (1994); Dore-Duffy et al., *Frontiers in Cerebral Vascular Biology: Transport and Its Regulation,* 243-248 (Eds. Drewes & Betz, Plenum, N.Y. 1993)).

The interaction between α4β1 and its targets is a component of the inflammation that takes place in the CNS of patients with multiple sclerosis (MS). Under normal conditions, VCAM-1 is not expressed in the brain parenchyma. However, in the presence of pro-inflammatory cytokines, VCAM-1 is upregulated on endothelial cells and on microglial cells near the sites of inflammation (Elices et al., *Cell* 60:577-584 (1990); Lobb and Hemler, *J. Clin. Invest.* 94:1722-1728 (1994); Peterson et al., *J. Neuropathy Exp. Neurol.* 61:539-546 (2002)). Further, osteopontin, which exhibits many properties of a proinflammatory cytokine, is also upregulated in MS lesions (Chabas et al., *Science* 294:1731-1735 (2001)).

MS is a serious and disabling inflammatory and autoimmune disease of young adults, with a peak age of onset in the third decade of life. Most individuals present with the relapsing-remitting form of the disease and experience recurrent attacks, which, over time, result in accumulating permanent physical disability and cognitive decline. About 70% of these individuals will eventually enter a phase of progressive neurological decline (secondary progressive MS), with or without superimposed relapses. Current treatments are minimally effective for secondary progressive MS. The majority of patients suffer permanent neurological dysfunction and, on average, have a life expectancy of six to seven years after the onset of disease.

Currently, four therapies are approved in the United States for the treatment of relapsing forms of MS. The interferons, Betaseron® (interferon β-1b SC (subcutaneous)), AVONEX® (interferon β-1a IM (intramuscular)), and Rebif® (interferon β-1a SC), are cytokines with antiviral, antiproliferative, and immunomodulatory activities. Copaxone® (glatiramer acetate) is a mixture of synthetic polypeptides with a poorly understood mechanism of action. The β-interferons can produce serious adverse events and some evidence suggests that copaxone is ineffective (Munari, et al., *The Cochrane Library,* Issue 1, Chichester, UK: John Wiley & Sons, Ltd. (2004)).

Serious adverse events of β-interferons include rare reports of hypersensitivity reactions, depression and suicide, decreased peripheral blood counts, hepatic injury, cardiomyopathy, and various autoimmune disorders (Betaseron Package Insert, 2003; Rebif Package Insert, 2004; AVONEX® Package Insert, 2005). The development of neutralizing antibodies to interferons is associated with a loss of efficacy. Antibodies that develop to a β-interferon cross-react with other interferons leading to loss of efficacy for the entire class in such patients (IFNB MS Study Group, *Neurology* 47:889-894 (1996); PRISMS Study Group, *Neurology* 56:1628-1636 (2001); Kappos et al., *Neurology* 65:40-47 (2005)). As a result, in the United States alone, over 50,000 patients who were previously treated no longer receive therapy. Thus, there is a large group of patients with active MS who are currently not receiving any approved therapy.

Among those patients who do receive treatment, a significant number continue to experience disease activity, as observed clinically and by magnetic resonance imaging (MRI). Although a variety of therapeutic strategies are currently used in clinical practice to manage breakthrough disease while on treatment (e.g., switching therapy, changing dose and frequency of interferon, combination therapy), the similar efficacy between available medications and lack of clinical data demonstrating the effectiveness of any of these strategies in breakthrough patients makes the decision of what to do for these patients largely empirical. Each of the partially effective approved medications leads to an approximately 30% reduction in relapse rate and limited impact on disability progression (IFNB MS Study Group, *Neurology* 43:655-661 (1993); Jacobs et al., *Ann. Neurol.* 39:285-289 (1996); PRISMS Study Group, *Lancet* 352:1498-1504 (1998)); Johnson et al., *Neurology* 45:1268-1276 (1995)). Data from the Phase 3 trials of β-interferon in MS show that 62% to 75% of subjects experienced at least one relapse during these 2-year trials despite interferon treatment (IFNB MS Study Group, *Neurology* 43:655-661 (1993); Jacobs et al., *Ann. Neurol.* 39:285-289 (1996); PRISMS Study Group, *Lancet* 352:1498-1504 (1998)). Similarly, 66% of subjects in the Phase 3 MS trial of glatiramer acetate experienced at least one relapse during the 2-year period, a proportion that was not significantly different from placebo (Johnson et al., *Neurology* 45:1268-1276 (1995)).

Progressive Multifocal Leukoencephalopathy (PML) is a severe, rapidly progressive disease that destroys the myelin coating which protects nerve cells. PML occurs almost exclusively in severely immunosuppressed patients and is frequently associated with lymphoproliferative and other chronic diseases, such as AIDS, Hodgkin's disease, chronic lymphocytic leukemia, sarcoidosis, tuberculosis, systemic lupis erythematosis, and organ transplantation. JC virus (JCV) is the etiological agent of PML and may result from a primary infection or follow reactivation of latent virus.

Natalizumab, an α4-integrin antagonist, has been used successfully to treat diseases with inflammatory and/or autoimmune components, for example, MS, Crohn's Disease, and rheumatoid arthritis. There are three known cases of PML occurring during or after administration of natalizumab, two proved fatal and one patient recovered. All three cases occurred in patients on concomitant medications which may have contributed to immunosuppression.

Thus, there is a need in the art for determining the relationship between natalizumab treatment and the occurrence of PML and for safer methods of treating patients with natalizumab that take into account the possibility of contracting PML.

SUMMARY

The invention provides safer methods of using natalizumab to treat patients with inflammatory and autoimmune diseases.

In a first aspect, the invention provides a method of using natalizumab to treat a patient with an inflammatory or autoimmune disease by administering a pharmaceutically effective amount of natalizumab; monitoring the patient for indicators of progressive, multifocal leukoencephalopathy; and discontinuing the administration of natalizumab in the presence of indicators of progressive multifocal leukoencephalopathy; wherein the monitoring improves the safety of the treatment. In embodiments of the method the disease is multiple sclerosis. In embodiments the multiple sclerosis is selected from relapsing remitting, secondary progressive, primary progressive, and chronic progressive multiple sclerosis. In embodiments of the method the disease is inflammatory bowel disease or rheumatoid arthritis. In embodiments the inflammatory bowel disease is Crohn's Disease. In embodiments of the method the monitoring detects JCV in the patient's urine, blood, and/or cerebrospinal fluid, and in embodiments of such methods the monitoring comprises serially removing samples of the patient's blood, measuring the amount of IgG antibodies to JCV in the samples, and comparing the amount of the antibodies in the samples.

In embodiments the method includes measuring the amount of IgM antibodies to JCV in the samples, and comparing the amount of the IgM and IgG antibodies in the samples. In embodiments the monitoring detects seroconversion and/or an increasing titer of JCV in the patient's urine and/or blood, and further includes removing a sample of the patient's cerebrospinal fluid when the comparison of the serial urine and/or blood samples detect seroconversion and/or an increasing titer of JCV; and testing the cerebrospinal fluid for the presence of JCV.

In embodiments of the method, the monitoring comprises testing for clinical and/or radiologic symptoms of progressive multifocal leukoencephalopathy. In embodiments the testing for clinical symptoms comprises testing for new or worsening neurological symptoms. In embodiments the neurological symptoms comprise one or more of central blindness, mental confusion, personality change, and dyskinesia. In embodiments the testing for radiologic symptoms comprises performing a Gd-enhanced magnetic resonance imaging scan.

In embodiments the method includes, in the presence of indicators of progressive multifocal leukoencephalopathy, providing at least one treatment selected from intravenous immunoglobulin therapy, plasmapheresis, and antiviral therapy. In embodiments the antiviral therapy comprises the administration of at least one therapeutically effective dose of an antiviral agent selected from cytosine arabinoside (cytarabine), cidofovir, and a serotonin antagonist. In embodiments of the method, the serotonin antagonist is a 5HT2a antagonist.

In embodiments of the method the patient is not treated simultaneously with natalizumab and an immunosuppressive or antineoplastic agent. In embodiments the immunosuppressive or antineoplastic agent is selected from one or more of chlorambucil, melphalan, 6-mercaptopurine, thiotepa, ifodfamide, dacarbazine, procarbazine, temozolomide, hexamethylmelamine, doxorubicine, daunarubicine, idarubicin, epirubicin, irinotecan, methotrexate, etoposide, vincristine, vinblastine, vinorelbine, cytarabine, busulfan, amonifide, 5-fluorouracil, topotecan, mustargen, bleomycin, lomustine, semustine, mitomycin C, mutamycin, cisplatin, carboplatin, oxaliplatin, methotrexate, trimetrexate, raltitrexid, fluororodeoxyuridine, capecitabine, ftorafur, 5-ethynyluracil, 6-thioguanine, cladribine, pentostatin, teniposide, mitoxantrone, losoxantrone, actinomycin D, vindesine, docetaxel, amifostine, interferon alpha, tamoxefen, medroxyprogesterone, megestrol, raloxifene, letrozole, anastrzole, flutamide, bicalutamide, retinoic acids, arsenic trioxide, rituximab, CAMPATH-1, mylotarg, mycophenolic acid, tacrolimus, glucocorticoids, sulfasalazine, glatiramer, fumarate, laquinimod, FTY-720, interferon tau, daclizumab, infliximab, IL10, anti-IL2 receptor antibody, anti-IL-12 antibody, anti-IL6 receptor antibody, CDP-571, adalimumab, entaneracept, leflunomide, anti-interferon gamma antibody, abatacept, fludarabine, cyclophosphamide, azathioprine, cyclosporine, intravenous immunoglobulin, 5-ASA (mesalamine), and a β-interferon.

In another aspect the invention provides a method of using natalizumab to treat a patient with an inflammatory or autoimmune disease by removing a sample of blood from the patient; testing the serum or plasma of the sample for the presence of IgG antibodies to JCV; initiating treatment of the patient with natalizumab in the event the sample is negative for IgG antibodies to JCV; monitoring the patient for indicators of progressive multifocal leukoencephalopathy; and discontinuing the administration of natalizumab in the presence of indicators of progressive multifocal leukoencephalopathy; wherein the testing and monitoring improve the safety of the treatment. In embodiments of the method the disease is multiple sclerosis. In embodiments the multiple sclerosis is selected from relapsing remitting, secondary progressive, primary progressive, and chronic progressive multiple sclerosis. In embodiments of the method the disease is inflammatory bowel disease or rheumatoid arthritis. In embodiments the inflammatory bowel disease is Crohn's Disease. In embodiments the method further includes testing the serum or plasma of the sample for IgM antibodies to JCV and initiating treatment if the serum or plasma is negative for both IgG and IgM antibodies to JCV. In embodiments of the method the monitoring detects JCV in the patient's urine, blood, and/or cerebrospinal fluid. In embodiments of such methods the monitoring comprises serially removing samples of the patient's blood, measuring the amount of IgG antibodies to JCV in the samples, and comparing the amount of the antibodies in the samples. In embodiments the monitoring further comprises measuring the amount of IgM antibodies to JCV in the samples, and comparing the amount of the IgM and IgG antibodies in the samples. In embodiments the monitoring detects seroconversion and/or an increasing titer of JCV in the patient's urine and/or blood by removing a sample of the patient's cerebrospinal fluid when the comparison of the serial urine and/or blood samples detect seroconversion and/or an increasing titer of JCV; and testing the cerebrospinal fluid for the presence of JCV. In embodiments of the method the monitoring comprises testing for clinical and/or radiologic symptoms of progressive multifocal leukoencephalopathy. In embodiments the testing for clinical symptoms comprises testing for new or worsening neurological symptoms. In embodiments the neurological symptoms comprise one or more of central blindness, mental confusion, personality change, and dyskinesia. In embodiments the testing for radiologic symptoms comprises performing a Gd-enhanced magnetic resonance imaging scan.

In embodiments, the method further includes, in the presence of indicators of progressive multifocal leukoencephalopathy, providing at least one treatment selected from intravenous immunoglobulin therapy, plasmapheresis, and antiviral therapy. In embodiments the antiviral therapy comprises the administration of at least one therapeutically effective dose of an antiviral agent selected from cytosine arabinoside (cytarabine), cidofovir, and a serotonin antagonist. In embodiments the serotonin antagonist is a 5HT2a antagonist.

In embodiments of the method the patient is not treated simultaneously with natalizumab and an immunosuppressive or antineoplastic agent. In embodiments the immunosuppressive or antineoplastic agent is selected from one or more of chlorambucil, melphalan, 6-mercaptopurine, thiotepa, ifodfamide, dacarbazine, procarbazine, temozolomide, hexamethylmelamine, doxorubicine, daunarubicine, idarubicin, epirubicin, irinotecan, methotrexate, etoposide, vincristine, vinblastine, vinorelbine, cytarabine, busulfan, amonifide, 5-fluorouracil, topotecan, mustargen, bleomycin, lomustine, semustine, mitomycin C, mutamycin, cisplatin, carboplatin, oxaliplatin, methotrexate, trimetrexate, raltitrexid, fluororodeoxyuridine, capecitabine, ftorafur, 5-ethynyluracil, 6-thioguanine, cladribine, pentostatin, teniposide, mitoxantrone, losoxantrone, actinomycin D, vindesine, docetaxel, amifostine, interferon alpha, tamoxefen, medroxyprogesterone, megestrol, raloxifene, letrozole, anastrzole, flutamide, bicalutamide, retinoic acids, arsenic trioxide, rituximab, CAMPATH-1, mylotarg, mycophenolic acid, tacrolimus, glucocorticoids, sulfasalazine, glatiramer, fumarate, laquinimod, FTY-720, interferon tau, daclizumab, infliximab, IL10, anti-IL2 receptor antibody, anti-IL-12 antibody, anti-IL6 receptor antibody, CDP-571, adalimumab, entaneracept, leflunomide, anti-interferon gamma antibody, abatacept, fludarabine, cyclophosphamide, azathioprine, cyclosporine, intravenous immunoglobulin, 5-ASA (mesalamine), and a β-interferon.

In another aspect the invention provides a method of administering natalizumab to a patient with an inflammatory or autoimmune disease by removing a sample of blood from the patient; testing the serum or plasma of the sample for the presence of IgG antibodies to JCV; initiating treatment of the patient with natalizumab in the event the sample is positive for IgG antibodies to JCV; monitoring the patient for indicators of progressive multifocal leukoencephalopathy; and discontinuing the administration of natalizumab in the presence of indicators of progressive multifocal leukoencephalopathy; wherein the testing and monitoring improves the safety of the treatment. In embodiments of the method the disease is multiple sclerosis. In embodiments the multiple sclerosis is selected from relapsing remitting, secondary progressive, primary progressive, and chronic progressive multiple sclerosis. In embodiments of the method the disease is inflammatory bowel disease or rheumatoid arthritis. In embodiments the inflammatory bowel disease is Crohn's Disease. In embodiments of the method the monitoring detects JCV in the patient's urine, blood, and/or cerebrospinal fluid. In embodiments the monitoring comprises serially removing samples of the patient's blood, measuring the amount of IgG antibodies to JCV in the samples, and comparing the amount of the antibodies in the samples. In embodiments the monitoring detects an increasing titer of JCV in the patient's urine and/or blood, and further includes removing a sample of the patient's cerebrospinal fluid when the comparison of the serial urine and/or blood samples detect an increasing titer of JCV; and testing the cerebrospinal fluid for the presence of JCV. In embodiments of the method the monitoring comprises testing for clinical and/or radiologic symptoms of progressive multifocal leukoencephalopathy. In embodiments the testing for clinical symptoms comprises testing for new or worsening neurological symptoms. In embodiments the neurological symptoms comprise one or more of central blindness, mental confusion, personality change, and dyskinesia. In embodiments the testing for radiologic symptoms comprises performing a Gd-enhanced magnetic resonance imaging scan.

In embodiments the method further includes, in the presence of indicators of progressive multifocal leukoencephalopathy, providing at least one treatment selected from intravenous immunoglobulin therapy, plasmapheresis, and antiviral therapy. In embodiments the antiviral therapy comprises the administration of at least one therapeutically effective dose of an antiviral agent selected from cytosine arabinoside (cytarabine), cidofovir, and a serotonin antagonist. In embodiments the serotonin antagonist is a 5HT2a antagonist.

In embodiments of the method the patient is not treated simultaneously with natalizumab and an immunosuppressive or antineoplastic agent. In embodiments the immunosuppressive or antineoplastic agent is selected from one or more of chlorambucil, melphalan, 6-mercaptopurine, thiotepa, ifodfamide, dacarbazine, procarbazine, temozolomide, hexamethylmelamine, doxorubicine, daunarubicine, idarubicin, epirubicin, irinotecan, methotrexate, etoposide, vincristine, vinblastine, vinorelbine, cytarabine, busulfan, amonifide, 5-fluorouracil, topotecan, mustargen, bleomycin, lomustine, semustine, mitomycin C, mutamycin, cisplatin, carboplatin, oxaliplatin, methotrexate, trimetrexate, raltitrexid, fluororodeoxyuridine, capecitabine, ftorafur, 5-ethynyluracil, 6-thioguanine, cladribine, pentostatin, teniposide, mitoxantrone, losoxantrone, actinomycin D, vindesine, docetaxel, amifostine, interferon alpha, tamoxefen, medroxyprogesterone, megestrol, raloxifene, letrozole, anastrzole, flutamide, bicalutamide, retinoic acids, arsenic trioxide, rituximab, CAMPATH-1, mylotarg, mycophenolic acid, tacrolimus, glucocorticoids, sulfasalazine, glatiramer, fumarate, laquinimod, FTY-720, interferon tau, daclizumab, infliximab, IL10, anti-IL2 receptor antibody, anti-IL-12 antibody, anti-IL6 receptor antibody, CDP-571, adalimumab, entanercept, leflunomide, anti-interferon gamma antibody, abatacept, fludarabine, cyclophosphamide, azathioprine, cyclosporine, intravenous immunoglobulin, 5-ASA (mesalamine), and β-interferon.

In another aspect the invention provides a method of using natalizumab to treat a patient with an inflammatory or autoimmune disease by removing a sample of blood from the patient; testing the sample for the presence of IgG antibodies to JCV; initiating treatment of the patient with natalizumab; informing the prescribing physician about the mental and physical symptoms of progressive multifocal leukoencephalopathy; informing the patient about the mental and physical symptoms of progressive multifocal leukoencephalopathy and instructing the patient to report to the physician in the presence of at least one symptom; monitoring the patient for indicators of progressive multifocal leukoencephalopathy; and discontinuing the administration of natalizumab in the presence of indicators of progressive multifocal leukoencephalopathy; wherein the testing, information, and monitoring improve the safety of the treatment. In embodiments of the method the disease is multiple sclerosis. In embodiments the multiple sclerosis is selected from relapsing remitting, secondary progressive, primary progressive, and chronic progressive multiple sclerosis. In embodiments of the method the disease is inflammatory bowel disease or rheumatoid arthritis. In embodiments the inflammatory bowel disease is Crohn's Disease. In embodiments of the method the monitoring detects JCV in the patient's urine, blood, and/or cerebrospinal fluid. In embodiments the monitoring comprises serially removing samples of the patient's blood, measuring the amount of IgG antibodies to JCV in the samples, and comparing the amount of the antibodies in the samples. In embodiments the monitoring further comprises measuring the amount of IgM antibodies to JCV in the samples, and comparing the amount of the IgM and IgG antibodies in the samples. In embodiments the monitoring detects seroconversion and/or an increasing titer of JCV in the patient's urine and/or blood, and further includes removing a sample of the patient's cerebrospinal fluid when the comparison of the serial urine and/or blood samples detect seroconversion and/or an increasing titer of JCV; and testing the cerebrospinal fluid for the presence of JCV.

In embodiments of the method the monitoring comprises testing for clinical and/or radiologic symptoms of progressive multifocal leukoencephalopathy. In embodiments the testing for clinical symptoms comprises testing for new or worsening neurological symptoms. In embodiments the neurological symptoms comprise one or more of central blindness, mental confusion, personality change, and dyskinesia. In embodiments the testing for radiologic symptoms comprises performing a Gd-enhanced magnetic resonance imaging scan.

In embodiments the method further includes, in the presence of indicators of progressive multifocal leukoencephalopathy, providing at least one treatment selected from intravenous immunoglobulin therapy, plasmapheresis, and antiviral therapy. In embodiments the antiviral therapy comprises the administration of at least one therapeutically effective dose of an antiviral agent selected from cytosine arabinoside (cytarabine), cidofovir, and a serotonin antagonist. In embodiments the serotonin antagonist is a 5HT2a antagonist.

In embodiments of the method the patient is not treated simultaneously with natalizumab and an immunosuppressive or antineoplastic agent. In embodiments the immunosuppressive or antineoplastic agent is selected from one or more of chlorambucil, melphalan, 6-mercaptopurine, thiotepa, ifodfamide, dacarbazine, procarbazine, temozolomide, hexamethylmelamine, doxorubicine, daunarubicine, idarubicin, epirubicin, irinotecan, methotrexate, etoposide, vincristine, vinblastine, vinorelbine, cytarabine, busulfan, amonifide, 5-fluorouracil, topotecan, mustargen, bleomycin, lomustine, semustine, mitomycin C, mutamycin; cisplatin, carboplatin, oxaliplatin, methotrexate, trimetrexate, raltitrexid, fluororodeoxyuridine, capecitabine, ftorafur, 5-ethynyluracil, 6-thioguanine, cladribine, pentostatin, teniposide, mitoxantrone, losoxantrone, actinomycin D, vindesine, docetaxel, amifostine, interferon alpha, tamoxefen, medroxyprogesterone, megestrol, raloxifene, letrozole, anastrzole, flutamide, bicalutamide, retinoic acids, arsenic trioxide, rituximab, CAMPATH-1, mylotarg, mycophenolic acid, tacrolimus, glucocorticoids, sulfasalazine, glatiramer, fumarate, laquinimod, FTY-720, interferon tau, daclizumab, infliximab, IL10, anti-IL2 receptor antibody, anti-IL-12 antibody, anti-IL6 receptor antibody, CDP-571, adalimumab, entaneracept, leflunomide, anti-interferon gamma antibody, abatacept, fludarabine, cyclophosphamide, azathioprine, cyclosporine, intravenous immunoglobulin, 5-ASA (mesalamine), and a β-interferon.

DETAILED DESCRIPTION OF THE INVENTION

Brief Description of the Embodiments
Definitions

The terms used herein have their ordinary meanings, as set forth below, and can be further understood in the context of the specification.

A "patient" or "subject," used interchangeably herein, is a human unless otherwise indicated.

"Treatment" means any administration or application of remedies for disease and includes inhibiting the disease, arresting its development, and relieving the disease, for example, by causing regression, or restoring or repairing a lost, missing, or defective function or by stimulating an inefficient process.

"Natalizumab" or "Natalizumab®" is a humanized antibody against VLA-4 as described in U.S. Pat. Nos. 5,840, 299 and 6,033,665, which are herein incorporated by reference in their entireties. Also contemplated herein are other antibodies specific for VLA-4, including, but not limited to, immunoglobulins described in U.S. Pat. Nos. 6,602,503 and 6,551,593, and published U.S. Application No. 20020197233 by Relton et al. These antibodies can be prepared by the methods disclosed in these documents, by mammalian cell expression systems, and by transgenic animal expression systems, for example, transgenic goats.

A "pharmaceutically effective amount" or "therapeutically effective amount," used interchangeably, is an amount sufficient to cure or at least partially arrest the symptoms of a disease and/or the complications of a disease.

A "serotonin antagonist" is any substance that decreases one or more effect of serotonin.

"Seroconversion" is the change of a serologic test from negative to positive, indicating the development of antibodies.

"Titer" is the concentration of an antibody in solution.

Natalizumab

Natalizumab is a humanized $IgG_4\kappa$ monoclonal antibody directed against the α4-integrins α4β1 and α4β7. Studies by Yednock and others have shown the clinical efficacy of α4-integrin blockade in experimental allergic encephalomyelitis (EAE), an animal model of MS (Yednock et al., *Nature* 1992; 356:63-66 (1992); Baron et al., *J. Exp. Med.* 177:57-68 (1993); Kent et al., *J. Neuroimmunol.* 58:1-10 (1995); Brocke et al., *Proc. Natl. Acad. Sci.* 96:6896-6901 (1999). These data demonstrated that α4-integrin blockade by a bound antibody can prevent leukocyte migration into the brain and thus support the hypothesis that α4-integrins area target for MS therapeutics. In addition, these observations support the hypothesis that blockading leukocyte accumulation in the brain will prevent the local destruction of myelin, the insulating sheath covering nerve fibers, and neurons, which characterizes MS lesions. Natalizumab is the first antibody directed at this target and clinical data demonstrate the relevance of this treatment strategy.

Natalizumab is a member of an emerging class of agents known as the Selective Adhesion Molecule (SAM) Inhibitors. Natalizumab binding to β4β1 (also called VLA-4) and β4β7 integrins inhibits their molecular interactions with cognate integrin receptors on endothelial cells, VCAM-1 and MAdCAM-1, respectively. By inhibiting these molecular interactions, natalizumab prevents the recruitment and egress of leukocytes into sites of inflammation. A further mechanism of natalizumab action may be to suppress ongoing inflammatory reactions in diseased tissues by inhibiting the interaction of α4-expressing leukocytes with other ligands in the extracellular matrix (osteopontin and fibronectin) and on parenchymal cells, such as microglial cells (VCAM-1). As such, natalizumab may suppress ongoing inflammatory activity at the disease site and inhibit further recruitment of immune cells into inflamed tissues. Thus, treating MS patients with natalizumab may block entry of mononuclear leukocytes into the CNS and attenuate the inflammatory process that results in demyelination and axonal damage and ultimately provide clinical benefit by reducing the number of clinical relapses and the progression of disability, including motor, visual, and cognitive function.

Safety of Natalizumab

The safety of natalizumab is demonstrated herein, based on results of treating 3,919 subjects with natalizumab in clinical trials for MS, Crohn's Disease, and rheumatoid arthritis, resulting in 5,505 patient-years of natalizumab exposure. Treatment with natalizumab was generally well tolerated. Eighteen treatment-emergent deaths occurred in the entire natalizumab program. The adverse events encountered in the trials, both common and serious, were similar in natalizumab-treated patients and controls. Adverse events that led to discontinuation of natalizumab occurred in 5.8% of natalizumab-treated MS patients and in 4.8% of placebo-treated MS patients, with urticaria being the most common cause of discontinuation in the natalizumab-treated patients (1.2%).

Like other highly active drugs used to treat autoimmune diseases, natalizumab is not without risk. Unfortunately, with the clinical efficacy of immunomodulatory agents such as natalizumab comes the risk of significant mechanism-based side effects. The risks of medications that modulate immune function in order to treat serious chronic diseases have been well recognized over the past several years. Medicines such as the TNFα antagonists (e.g., infliximab, adalimumab, and etanercept) are potent modulators of immune function and are approved for numerous serious autoimmune diseases such as rheumatoid arthritis; Crohn's Disease, psoriasis, psoriatic arthritis, and ankylosing spondylitis. Although very effective, these agents are associated with serious adverse events, particularly infections that have been associated with significant morbidity and mortality.

The invention provides the identification, through detailed safety analyses, of PML as a rare, but significant, risk of natalizumab treatment. In addition, serious non-PML opportunistic infections have been observed in natalizumab-treated patients, mostly in Crohn's Disease patients in association with concurrent immunosuppressant use or other significant co-morbidities. In addition, we have identified patient populations in whom the benefit-risk profile is less well defined. The occurrence of these infections highlights the need for a comprehensive risk management program in the post-marketing setting focused on appropriate use conditions and assessment and minimization of the risk of PML and other serious opportunistic infections.

Deaths

Of the eighteen deaths that occurred during the clinical trials, five occurred in the placebo-controlled MS trials, including two in patients who had received natalizumab and three who had received placebo). The patients who received natalizumab died of alcohol intoxication and metastatic malignant melanoma. The patients who received placebo died of cardiac arrest, respiratory arrest, and pleural carcinomatosis with seizures. Four deaths occurred in the open-label MS trials, due to respiratory distress, PML, suicide, and seizure due to MS.

Six deaths of natalizumab-treated Crohn's Disease patients were observed in the trials. The exposure to natalizumab was approximately three-fold greater in these trials than exposure to placebo. The causes of death were acute myocardial infarction, acute renal failure, carbon dioxide asphyxiation, PML, *pneumocystis carinii* pneumonia, and bronchopulmonary aspergillosis.

Three deaths occurred in the rheumatoid arthritis trials, two in natalizumab-treated patients and one in a patient treated with a placebo. The natalizumab-treated patients died of hemoptysis with respiratory failure and end-stage rheumatoid pulmonary disease. The placebo-treated patient died of circulatory and respiratory insufficiency.

In the MS studies, apart from PML, no other safety signal was apparent from the study deaths. In the Crohn's Disease studies, one patient died from PML. Two additional deaths in Crohn's Disease were associated with opportunistic infections, namely, bronchopulmonary aspergillosis and *pneumocystis carinii* pneumonia. These patients had significant co-morbidities, which may have contributed to the development of these infections.

Adverse Events

At least one serious adverse event was encountered by 251 of the 1,617 natalizumab-treated MS patients (15.5%) and by 214 of the 1,135 placebo-treated patients (18.9%) in the placebo-controlled trial. The most common serious adverse events, classified by organ systems, were nervous system disorders (5.9% natalizumab, 10.2% placebo). MS relapse contributed significantly to this incidence (4.7% natalizumab, 9.0% placebo). The second most common serious adverse events were infections and infestations (2.4% natalizumab, 2.2% placebo), with appendicitis and urinary tract infection (<1% in both groups) as the most common.

The incidence of hypersensitivity reactions, an event expected to result from treatment with therapeutic proteins, was approximately 4% with serious systemic reactions occurring at an incidence of less than 1%. The reactions tended to occur early in the treatment course, but were observed throughout the course of infusion. Although the specific mechanisms of the reactions have not been determined, clinically, the reactions appeared to be typical IgE- or IgG-mediated immediate-type hypersensitivity reactions. All patients recovered without sequelae.

The occurrence of malignancy during natalizumab treatment was uncommon. The incidence of malignancy was balanced between the natalizumab and control groups. The rates of malignancies observed during natalizumab treatment were within the expected rates per comparison with the existing cancer registries, such as the National Cancer Institute's Surveillance Epidemiology and End Results.

Evaluation of PML Cases

Three confirmed cases of PML have been identified, two of which were fatal. Two cases occurred in MS patients and one in a patient with Crohn's Disease. Both MS patients received natalizumab for over two years in addition to AVONEX®. The Crohn's Disease patient received eight doses of natalizumab over an 18-month period and was immunocompromised due to chronic azathioprine use as manifested by persistent lymphopenia. All three PML patients presented with subtle clinical changes early in their disease course that were noted by the patients or their families.

The first patient to contract a fatal case of PML was a 46-year-old female with MS who presented to her neurologist with right-sided paresthesia and dysesthesia, and right upper extremity clumsiness. MRI brain scanning demonstrated four non-enhancing T2-hyperintense lesions bilaterally in the corona radiata. Six weeks later, she presented with new blurring of the vision in her right eye. Visual acuity was 20/15 in the left eye and 20/100 in the right. Spinal fluid analysis yielded one white blood cell, normal protein and glucose, and no oligoclonal bands. A follow-up MRI brain scan revealed two new subcortical lesions in the right parietal region that were hyperintense on FLAIR imaging and hypointense on T1.

AVONEX® treatment was initiated, but she subsequently suffered three relapses, the most recent of which involved band-like pain around the abdomen, lower extremity weakness, and spasticity requiring treatment with methylprednisolone. Her Expanded Disability Status Scale (EDSS) score in prior to entry into the placebo-controlled MS study, as described in more detail below, was 2.5. She received 30 infusions of natalizumab before entering the open-label extension study and receiving an additional seven infusions. She had no exacerbations or suspected relapses during her time in the placebo-controlled study. She developed five new or enlarging T2-hyperintense lesions during the first year of the placebo-controlled study and one during the second year. She was negative for anti-natalizumab antibodies and her serum concentration of natalizumab was similar to the mean of the study populations throughout her participation.

In November 2004, she began to experience motor dysfunction, and cognitive and language difficulties, which progressed to right hemiparesis by the following month. An MRI brain scan performed in December 2004 revealed left frontal T2-hyperintensity and T1-hypointensity with extension into the centrum semiovale and corona radiata without Gd-enhancement. She received two courses of high dose steroids over the next few months; but continued to decline. She received her last dose of natalizumab on Jan. 18, 2005. She was readmitted to the hospital on Feb. 12, 2005 with worsening clinical status. A repeat MRI brain scan in February 2005 showed extension of the lesion seen previously. An extensive work-up over the next week revealed JC viral DNA in the CSF, resulting in the diagnosis of PML. She died on Feb. 24, 2005. Post-mortem examination revealed normal organs without evidence of opportunistic infection. The brain examination revealed extensive, severe cavitation mainly in the left hemisphere as well as multiple non-cavitated, ovoid areas throughout the white matter of both hemispheres typical of PML, having reactive astrocytes with enlarged, hyperchromatic nuclei (Kleinschmidt-DeMasters and Tyler, *N. Engl. J. Med.* 353:369-374 (2005)).

The second patient is a 46-year-old male who experienced his first symptoms of relapsing/remitting MS in 1983. His past medical history is significant for auricular zoster, Ramsay-Hunt syndrome, and melanoma. His family history is notable for a sister with MS. He had been treated with AVONEX® since 1998, and experienced three relapses the year before enrolling in the placebo-controlled MS study, during which he experienced no relapses or evidence of progression. He was negative for anti-natalizumab antibodies and his serum concentration of natalizumab was similar to the mean of the study populations throughout his participation.

In October 2004, his MRI scan showed a small periventricular Gd-enhancing lesion on the right and a small right frontal, subcortical, non-enhancing, T2-hyperintense lesion. In November 2004, he exhibited behavioral changes followed by hemiparesis and cognitive impairment. His last dose of natalizumab was in December 2004. In February 2005, despite treatment with high dose intravenous methylprednisolone, he continued to deteriorate. A brain MRI scan in February 2005 demonstrated extension of the previously identified lesion. He underwent an extensive work-up, including CSF analysis and brain biopsy, which resulted in the diagnosis of PML. Cidofovir treatment was initiated without clinical effect. The JC viral load decreased in his plasma and CSF over the next few months. This corresponded to further deterioration in his clinical course and development of Gd-enhancing lesions on MRI, consistent with Immune Reconstitution Inflammatory Syndrome. He continued to receive treatment with cidofovir, and cytarabine was added. Approximately 3 months following discontinuation of natalizumab, he began to improve. He is able to converse and can hold high-level conversations about his medical course and treatment, but has significant residual cognitive impairment with left hemiparesis and ataxia (Langer-Gould et al., *N. Eng. J. Med.* 353:375-381 (2005)).

The final patient was a 60-year-old male with a 28-year history of Crohn's Disease. Over the course of his illness, he had been treated with azathioprine, oral budesonide, corticosteroids, and four doses of infliximab. He displayed pre-existing signs of impaired hematopoiesis, predominantly lymphopenia and anemia, since 1996 and received azathioprine beginning in 1999. He was enrolled in a Phase 3 study of natalizumab in patients with active Crohn's Disease in March 2002 and received three doses concomitantly with azathioprine prior to being randomized to placebo in a Phase 3 maintenance study. He remained on azathioprine and placebo until November 2002 when azathioprine was discontinued due to refractory pancytopenia. In February 2003, he began open-label treatment with natalizumab. He was negative for anti-natalizumab antibodies and his serum concentration of natalizumab was similar to the mean of the study populations throughout his participation.

In July 2003, one month after his fifth dose of natalizumab, he presented with a one-week history of cognitive decline. A brain MRI scan demonstrated a large T2-hyperintense lesion in the right frontal lobe, and additional hyperintense lesions in the left frontal and temporal lobes that did not enhance with gadolinium. He underwent a partial resection of the lesion, the pathology of which was read at the time as an anaplastic astrocytoma, WHO Grade III. He was treated with corticosteroids and anticonvulsants, but was too ill for radiation therapy. Follow-up MRI six weeks after surgery showed tumor extension. He deteriorated clinically and died in December 2003. The case was reported by the treating physician as a malignant astrocytoma, based upon the final pathology report. In February, as a result of the one confirmed and one suspected case of PML described above, his case was reassessed and determined to be PML following consultation with two independent neuropathologists with expertise in PML (Van Assche et al., *N. Engl. J. Med.* 353:362-368 (2005)).

Clinical trial patients exposed to natalizumab were systematically assessed for evidence of incipient PML or any other opportunistic infection. Patients were evaluated if they had any active neurological deterioration for which PML could not be excluded as a diagnosis, showed MRI abnormalities for which PML could not be ruled out, or their CSF had detectable JCV DNA titers.

Criteria were established prospectively for the neuroradiologic evidence and laboratory assays for the diagnosis of PML. A diagnosis of "confirmed PML" was defined by presence of progressive clinical disease, MRI signs typical of PML, detection of JCV DNA in CSF; or pathologic confirmation. Sufficient evidence to exclude PML was defined as lack of progressive neurological disease, MRI lesions not typical of PML or stable over time, or no detectable JCV DNA in the CSF if the MRI was suspicious. A case was deemed "indeterminate" if there was clinical or MM suspicion of PML and follow-up clinical, MRI, or CSF data could not be obtained.

A total of 3,826 eligible study participants (2,248 MS patients, and 1,578 Crohn's Disease/rheumatoid arthritis patients) were notified to report to their treating physician/investigators for an assessment. Investigators were requested to perform the assessment procedure, including medical history, neurological examination, brain MRI, and CSF collection. Blood samples were also collected for PCR analysis of JCV DNA as an exploratory adjunct. MRI scans were assessed by Central Reader Centers with expertise in neurological disorders, including the two Central Reader Centers for the original Phase 3 MS studies. A consensus guideline was developed prospectively to standardize criteria to help distinguish MS white matter abnormalities from those of PML.

In all, 3,389 (89%) study patients with MS, Crohn's Disease, or rheumatoid arthritis were assessed by their treating physician, 3,116 of whom had received natalizumab. The remaining 273 patients had received placebo as part of a clinical trial and were included as a control group. Of the 437 that were not assessed, 60 (22 MS patients, 38 Crohn's Disease/rheumatoid arthritis patients) were lost to follow-up. Amongst the 3,389 patients who participated, 2,046 were MS study patients, over 97% of whom were seen within three months of their last natalizumab dose. Six MS patients were referred for further evaluation. Of these clinical trial patients, five were referred due to neurological worsening and one due to possible PML based on MRI findings. MRI scan review effectively ruled out the diagnosis of PML in the five patients referred based on clinical concern. Repeat MRI and CSF analysis excluded PML in the case referred based on MRI findings.

Of the 1,349 Crohn's Disease/rheumatoid arthritis patients who participated in the safety evaluation, 21% were seen within three months of their last dose, 91% within six months. Thirty-five patients were evaluated, including one due to clinical or neurological symptoms, 32 based on suspicious changes on MRI, one due to high plasma JCV copy number, and one due to an inability to perform MRI in a patient with a normal neurological examination. The higher rate of examination of Crohn's Disease compared to MS was predominantly driven by the lack of baseline MRI scans for comparison in the Crohn's Disease population. Most cases were deemed not to be PML based on review of neurological examination, MRI and, if available, CSF testing. For the ten cases in which concern still remained, repeat MRI assessments were performed and all were diagnosed as "not PML" based on lack of clinical progression, lack of MRI progression over two months following the initial MRI leading to referral for evaluation, and in some cases, results of CSF testing.

MRI scans of the brain with and without Gd-enhancement and a FLAIR sequence were sometimes a useful tool for excluding a diagnosis of PML in the MS cases. The existence of pre-treatment and on-treatment MRI scans increased specificity and assisted in interpretation of the follow-up MRI scans obtained at varying time points, especially in the setting when the patient's neurological condition was worsening. During the safety evaluation process, comparison to previous scan was required in approximately 35% percent of MS cases because of the presence of lesions for which PML could not be definitely excluded. After comparison to a prior scan, the neuroradiologist was able to exclude PML in greater than 99% of MS cases.

CSF was available for testing in 396 patients who had been treated for MS or Crohn's Disease with natalizumab. JCV was not detected in any of these cases, including 19 patients evaluated based on clinical or MRI criteria. Samples from 411 patients with MS and other neurological disorders served as CSF and plasma controls and were evaluated in collaboration with the Karolinska Institute and the National Institutes of Health (Yousry et al., *N. Engl. J. Med.* scheduled for publication Mar. 2, 2006). No detectable JCV was found in these CSF samples, confirming the specificity of the CSF assay for only active cases of PML. Each of the three patients with confirmed PML had detectable JCV DNA. A previous study had indicated that JCV was found in 11% of the biological specimens of the 121 MS patients tested (Ferrante et al., *Multiple Sclerosis* 4:49-54 (1998)).

Plasma was tested for the presence of JCV DNA as an exploratory measure. The entire consenting study population (2,370 patients) was evaluated using a high-throughput automated system of DNA extraction and PCR analysis. In addition, a random subset of samples was assessed using a manual low-throughput method. Although the manual method was demonstrated to be an order of magnitude more sensitive than the high-throughput system, given the techniques involved, testing using this method was only possible in approximately 10% of the overall population (209 patients). Of the 2,370 patients from the safety evaluation who were tested for JC viremia, only five patients (0.2%) had detectable JCV DNA, three of whom had never received natalizumab. In addition, JCV DNA was not detected in any of the 411 samples from MS patients naïve to treatment and patients with other neurological diseases. These results were confirmed using the manual extraction method. In addition, of the random subset of 209 patients tested by the manual method, an additional five (2.4%) samples had detectable JCV DNA. None of the patients with detectable JCV DNA in their plasma by either method had clinical features or MRI findings suggestive of PML.

Serum samples were available from the three patients with confirmed PML obtained both before and after diagnosis. Only one patient, the patient with Crohn's Disease, had detectable JCV DNA in the serum prior to the onset of his symptoms. The other two patients had no detectable JCV DNA despite being clinically symptomatic for the disease and manifesting changes on a brain MRI scan. The observations in these groups of patients are consistent with the data from the literature demonstrating that the mere presence of JCV DNA in plasma is neither predictive nor diagnostic of PML.

In summary, the comprehensive safety assessment performed following the identification of PML in natalizumab-treated patients uncovered no additional confirmed cases of PML in the over 3,000 patients examined. Nearly all patients who had received natalizumab in recent MS, Crohn's Disease, and rheumatoid arthritis studies were accounted for during the assessments, making it unlikely that any cases of PML were missed. The occurrence of PML was limited to two MS cases and one Crohn's Disease case, as originally described. The incidence of PML in subjects treated with natalizumab in MS and Crohn's Disease clinical trials is therefore approximately 1/1,000 with a 95% confidence interval ranging from 0.2 to 2.8/1,000. Plasma testing proved to be neither predictive nor diagnostic of PML, consistent with the published literature (Kitamura et al., *J. Infect. Dis.* 161:1128-1133 (1990); Tomatore et al., *Ann. Neurol.* 31:454-462 (1992); Dorries et al., *Virology* 198:59-70 (1994); Agostini et al., *J. Clin. Microbiol.* 34:159-164 (1996); Dubois et al., *AIDS* 10:353-358 (1996); Knowles et al., *J. Med. Virol.* 59:474-479 (1999); Dorries et al., *J. Neurovirol.* 9 (Suppl 1):81-87 (2003)). Clinical and MRI abnormalities were present in two of the three patients with PML before JCV DNA was detected in the plasma. In addition, JCV DNA was detected in plasma in several subjects in the study who had no clinical or radiographic signs of PML, including three who had never received natalizumab. These results suggest that establishing one static level of plasma JCV is not useful in predicting the likelihood of PML in asymptomatic patients. Physicians and patients should remain vigilant for signs and symptoms of PML and have a low threshold to suspend treatment and initiate appropriate diagnostic work-up (MRI, CSF analysis) in natalizumab-treated patients presenting with new neurological decline.

Consequences of Stopping Therapy

The consequences of stopping natalizumab therapy were carefully evaluated in a Phase 2 study, which involved 213 patients randomized to receive six monthly infusions of placebo, 3 mg/kg natalizumab, or 6 mg/kg natalizumab. Patients were followed for seven months after the last infusion. During that time, relapses and other adverse events were recorded, and MRI scans were performed four months and seven months after the last dose of natalizumab. Comparisons were made between the placebo group and the two natalizumab dosing groups. As expected, the proportion of patients experiencing relapse, as well as the frequency of relapses, rose in the natalizumab group to levels comparable to those in the placebo group after the cessation of study drug. Moreover, there was a gradual rise in the proportion of active MRI scans in the natalizumab group to levels comparable to that of the placebo group after the cessation of therapy. Thus, the cessation of natalizumab treatment resulted in loss of efficacy, but there was no evidence of an increase in disease activity beyond that which would have been expected had there been no treatment with natalizumab, i.e., no rebound effect was observed. Therefore, MS patients who discontinue natalizumab therapy do not have an increased risk for marked increase in disease activity.

Drug Interactions

In a placebo-controlled MS study, the administration of AVONEX® appeared to be associated with an increase in the serum concentrations of natalizumab in a small cohort on-whom intensive pharmacokinetic sampling was performed. However, based upon a comparison of the mean post-hoc parameter estimates from the population pharmacokinetic analysis, steady-state clearance and half-life values differed between patients concurrently taking AVONEX® and natalizumab monotherapy, but only by approximately 5%, and were not considered clinically significant. In addition, natalizumab was well tolerated when administered to 589 patients in combination with AVONEX® for up to 120 weeks. It is notable that the two reports of PML in the MS database occurred in patients receiving concomitant AVONEX®. Thus, the risk of PML with natalizumab treatment may be increased by concomitant treatment with interferon β, though this could have occurred in two patients on combination therapy due to chance alone (p=0.23).

The safety of natalizumab in combination with glatiramer acetate was evaluated by administering natalizumab over six months to patients who continued to receive 20 mg of daily glatiramer acetate. There were no interactions between glatiramer acetate and natalizumab pharmacokinetics or its α4-integrin receptor saturation. However, this study was of insufficient size or duration to establish the long-term safety or efficacy, in this population.

Efficacy of Natalizumab

Multiple Sclerosis

MS is a chronic disease of the brain and spinal cord. In temperate zones such as the United States, the incidence of MS is approximately 1 to 5/100,000 per year (US National MS Society; NMSS), with a US prevalence estimated at 350,000 to 400,000. It is a disease of young adults, primarily women, with disease onset typically occurring between the ages of 20 and 40. The first clinical manifestations of MS usually take the form of a clinically isolated syndrome affecting the optic nerve (optic neuritis), spinal cord (transverse myelitis), or brainstem/cerebellum (Runmarker and Anderson, *Brain* 116:117-134 (1993)). Estimates of the number of patients who eventually go on to develop MS vary widely, but, in the case of optic neuritis, the presence of MS-like lesions on MRI at the time of the attack indicates a greater than 80% chance of developing clinically definite MS within 10 years (O'Riordan et al., *Brain* 121:495-503 (1998); Sailer et al., *Neurology* 52:599-606 (1999)).

Demyelination and nerve fiber transection is thought to occur when activated T lymphocytes cross the blood-brain barrier and initiate a series of events leading to activation of endothelial cells, recruitment of additional lymphocytes and monocytes, and release of pro-inflammatory cytokines. MS lesions typically consist of immune cells, demyelinated axons, oligodendrocytes attempting remyelination, proliferating astrocytes, and varying degrees of axonal transection. Cytokines such as tumor necrosis factor-alpha (TNF-α) and interferon gamma (IFN-γ) interact with immune cells, amplifying this process. The initiating event of the inflammatory cascade is unknown; however, adhesion and trans endothelial migration of inflammatory cells from the bloodstream across the blood-brain barrier and into the central nervous system (CNS) is thought to be an early and critical step in this process.

Emerging data demonstrate that irreversible axonal loss occurs early in the course of MS. Because transected axons fail to regenerate in the CNS, early effective treatment aimed at suppressing MS lesion formation is of paramount importance. As early as disease onset, axons are transected in lesions with active inflammation (Trapp et al., *N. Engl. J. Med.* 338:278-285 (1998); Bjartmar and Trapp, *Curr. Opin. Neurol.* 14:271-278 (2001); Ferguson et al., *Brain* 120 (Pt 3):393-399 (1997)). The degree of demyelination is related to the degree of inflammation and the exposure of demyelinated axons to the inflammatory environment, as well as non-inflammatory mediators (Trapp et al., *N. Engl. J. Med.*; 338:278-285 (1998); Kornek et al., *Am. J. Pathol.* 157:267-276 (2000); Bitsch et al., *Brain* 123:1174-1183 (2000)). There is also destruction of oligodendrocytes with impaired remyelination in demyelinating lesions (Peterson et al., *J. Neuropathy Exp. Neurol.* 61:539-546 (2002); Chang et al., *J. Neurovirol.* 8:447-451 (2002)). The loss of oligodendrocytes leads to a reduction in the capacity to remyelinate and may result in the loss of trophic factors that support neurons and axons (Bjartmar et al., *J. Neurocytol.* 28:383-395 (1999)).

The typical inflammatory lesions of MS can occur throughout the CNS, but certain sites seem particularly vulnerable, such as the optic nerve, brainstem, spinal cord, and periventricular regions of the cerebrum. It is the resulting loss of myelin and nerve fibers in these areas that leads to impaired neuronal conduction and symptoms such as weakness, sensory loss, visual loss, double vision, and imbalance. In relapsing remitting MS, these episodes of demyelination typically result in several weeks of neurological dysfunction followed by partial or full recovery. However, more severe attacks may result in permanent deficits. The recurrent attacks over time lead to accumulating physical disability and cognitive decline.

A number of measures, including clinical measures, those based on MRI scans, and those based on quality of life, can be used to assess a product's efficacy in treating MS. The Expanded Disability Status Scale (EDSS) is an extensively used tool for tracking the course of disability in MS. It classifies the most common MS-associated neurological impairments into disability levels ranging from 0 to 10, with each successive step describing a worsening of disease. In the lower range of the EDSS scale, disease progression is primarily defined by increasing levels of disability in specific functional systems measured during neurological examination. Scores of 1.0 through 3.5 describe mild to moderate disability in the functional systems. Higher scores, in the range of 4.0 and above indicate increasingly severe disability that affects ambulation, including the need for assistive devices such as a cane (an EDSS of 6.0), a walker (an EDSS of 6.5), or a wheelchair (an EDSS of 7.0). Scores higher than 7.0 classify patients confined to bed.

The MS Functional Composite (MSFC) (Whitaker et al., *Multiple Sclerosis* 1:37-47 (1995)) is also used to assess efficacy. Unlike traditional MS clinical outcome measures that are derived from the standard neurological examination, the MSFC is based on quantitative tests of leg function/ambulation (the Timed 25-Foot Walk), arm function (the Nine-Hole Peg Test), and cognitive function (the Paced Auditory Serial Addition Test (PASAT 3)) which expand upon the measurements of the EDSS and assess effects in clinical dimensions not well captured by this scale.

MRI is another tool for assessing efficacy in treating MS and can be used alone or to support clinical data to assess therapeutic effects on relapse and disability endpoints. MRI is a sensitive tool for monitoring disease activity; detecting approximately five to ten times more disease activity in both relapsing remitting MS and secondary progressive MS patients than is clinically apparent (Isaac et al., *Neurology* 38:1511-1515 (1988); Willoughby et al., *Ann. Neurol.* 25:43-44 (1989); Khoury et al., *Neurology* 44:2120-2124 (1994); Thompson et al., *Ann. Neurol.* 9:53-62 (1991); Thompson et al., *Neurology* 42:60-63 (1992)). T2-weighted sequences in MS patients detect new areas of acute demyelination, as well as more chronic areas of demyelination and gliosis. For this reason; T2-weighted MRI is a good technique for monitoring the accumulation of lesions overtime, either as a count of active lesions or a change in the total volume of such lesions.

Infusion of gadolinium-diethylenetriamine pentaacetic acid (Gd-DPTA) during acquisition of T1-weighted sequences allows for visualization of blood-brain barrier breakdown secondary to the inflammation characteristic of acute MS lesions. The evidence to date suggests that gadolinium (Gd)-enhancement is a useful marker of disease activity that correlates with clinical relapse (Molyneux et al., *Ann. Neurol.* 43:332-339 (1998); Kappos et al., *Lancet* 353:964-969 (1999); McFarland et al., *Multiple Sclerosis* 8:40-51 (2002)).

New hypointense lesions on T1-weighted sequences in MS patients correspond either with inflammatory Gd-enhancing lesions (comprising edema, demyelination, axonal loss, or combinations of these pathologies) (Bruck et al., *Ann. Neurol.* 42:783-793 (1997)) or as chronic lesions with considerable axonal loss. Approximately half of the acute T1 hypointensities on MRI will evolve into chronic "T1 black holes," which correlate with disability progression (Simon et al., *Neurology* 55:185-192 (2000)).

As described in more detail in Example 1, two Phase 3 studies were conducted to study the effect of two years of treatment with natalizumab. One of the studies used natalizumab alone (the monotherapy study) and the other used natalizumab in combination with AVONEX® (the add-on therapy study). Both these Phase 3 studies were designed with two sets of primary and secondary endpoints. The primary and secondary endpoints were selected to measure the effects of natalizumab on the inflammatory aspects of the disease after a mean of one year of follow-up in each study (900 patient-years of observation in the monotherapy study; 1,200 patient-years in the add-on therapy study).

The primary endpoint of these studies was the annualized rate of clinical relapses. Two of the secondary endpoints were two supporting MRI measures of inflammatory disease activity, namely, the mean number of new or newly enlarging T2-hyperintense lesions (measuring lesion accumulation over time) and the mean number of Gd-enhancing lesions (measuring acute disease activity), as ranked in order of importance. The proportion of patients remaining relapse-free provided a third secondary endpoint.

Another series of endpoints was assessed at the conclusion of each study following two years of natalizumab treatment. The endpoints for this final analysis were selected to determine natalizumab's effects on measures associated with MS disease progression. The primary endpoint at two years was the time until onset of sustained progression of disability, as measured by changes in EDSS scores. Similar to the one-year analysis, the secondary endpoints were additional MRI and clinical measures that would support the primary analysis. The secondary endpoints at two years, ranked in order of importance, were the rate of MS relapses (to confirm one-year relapse observations), the mean volume of T2-hyperintense lesions (a measure of overall MS disease burden), the mean number of T1-hypointense lesions (a measure of axonal loss), and progression of disability as determined by changes in the MSFC (to confirm and expand upon disability effects as measured by the EDSS).

Given two primary endpoints at two different time points (annualized relapse rate at one year, time to disability progression at two years), the Hochberg procedure for multiple comparisons (Hochberg, *Biometrika* 75:800-802 (1988)) was used to evaluate the primary endpoint. Each set of secondary endpoints was prioritized in order of importance as listed above. A closed testing procedure was used for each set, such that if statistical significance was not achieved for an endpoint within a set, all endpoints(s) of a lower rank in that set were not considered statistically significant. Analyses of tertiary endpoints did not include adjustments for multiple comparisons.

Monotherapy with Natalizumab

These results of the monotherapy study indicated that natalizumab is an effective treatment as monotherapy for relapsing remitting MS. Natalizumab treatment resulted in significant effects on relapse rates, disability progression, and all MRI measures, the primary and secondary endpoints of the study. Analysis of Kaplan-Meier curves indicate that the impact on relapse rates and disability progression was apparent early after treatment initiation, and was sustained throughout the treatment period with patient groups continuing to diverge at the final timepoint. Further, these findings were consistent across subgroups. Additional positive effects were seen on measures of relapse severity and quality of life.

MS patients treated with natalizumab alone had a 42% lower risk of their disability progressing compared to placebo, as measured by changes on the EDSS, the primary endpoint of the study at two years (p<0.001). The percentage of patients estimated to progress was 17% and 29% with natalizumab and placebo, respectively. In addition to the EDSS, natalizumab had significant effects on all relapse endpoints studied over two years, including a 68% reduction in the annualized relapse rate compared to placebo, with 67% of natalizumab-treated patients remaining relapse-free, compared to 41% of patients on placebo. The MRI scans supported these clinically-observed effects. Also, natalizumab treatment improved the patients' quality of life, as measured by the physical and mental components of the SF-36. All these effects were consistent and significant across subgroups defined by baseline demographics and disease activity.

Combination Therapy of Natalizumab and AVONEX®

A significant number of patients who receive the currently approved therapies continue to experience disease activity, as measured both clinically and by MRI. This is an expected outcome of these partially effective approved medications, each of which leads to an approximately 30% reduction in relapse rate (IFNB MS Study Group, *Neurology* 43:655-661 (1993); Jacobs et al., *Ann. Neurol.* 39:285-289 (1996); PRISMS Study Group, *Lancet* 352:1498-1504 (1998); Johnson et al., *Neurology* 45:1268-1276 (1995)). Data from the Phase 3 trials of β-interferon for the treatment of MS show that 62% to 75% of patients experienced at least one relapse during these two-year trials despite interferon treatment IFNB MS Study Group, *Neurology* 43:655-661 (1993); Jacobs et al., *Ann. Neurol.* 39:285-289 (1996); PRISMS Study Group, *Lancet* 352:1498-1504 (1998)). Similarly, 66% of subjects in the Phase 3 MS trial of glatiramer acetate experienced at least one relapse during the 2-year period, a number that was not significantly different from placebo (Johnson et al., *Neurology* 45:1268-1276 (1995)). Although a variety of therapeutic strategies are currently in use in clinical practice to manage breakthrough disease while on treatment (e.g., switching therapy, changing dose and frequency of interferon, combination therapy), these practices are largely empirical as there are no randomized, controlled trials to assess the efficacy of these approaches.

The add-on therapy study was designed to evaluate the efficacy of natalizumab against active control for patients breaking through AVONEX® monotherapy. The choice of β-interferon was supported by available data on the proposed mechanisms of action of the available drugs. As discussed above, natalizumab has a well-defined mechanism of action, specifically targeting cellular adhesion and trans-endothelial migration via α4-integrins. Although the exact mechanism by which interferon-β exerts efficacy in MS is not known, interferon-β induces a large number of cellular processes involved in cytokine secretion and cellular phenotype changes. Interferon-β down regulates interferon-γ induced MHC class II molecule production, decreases secretion of TH1 pro-inflammatory cytokines (TNF-α, IL-2 and interferon-γ) and increases secretion of TH2 anti-inflammatory cytokines (IL-4 and IL-10) (Rep et al., *J. Neuroimmunol.* 67:111-118 (1996); Kozcivska et al., *Neurology* 53:1692-1697 (1999); Rudick et al., *Neurology* 50:1266-1272 (1998)). In addition, interferon-β may affect leukocyte trafficking through suppression of the chemokines RANTES and MIP-1α, as well as their receptor CCR5 (Zang et al., *J. Neuroimmunol.* 112:174-180 (2001)). There is, therefore, scientific rationale to expect that the blockade of α4-integrins by natalizumab, when added to interferon-β, may have an additive or synergistic effect when added to interferon-β alone.

Natalizumab was also proven efficacious when used to treat patients concurrently receiving treatment with AVONEX®. Prior to receiving natalizumab, these patients were experiencing disease activity despite active treatment. Thus, AVONEX® served as an active control. The study demonstrated that natalizumab, when added to AVONEX®, resulted in a 24% reduction in the risk of disability progression, as measured by changes on the EDSS (p=0.024). The percentage of patients estimated to progress was 23% with natalizumab plus AVONEX® as compared with 29% on AVONEX® alone.

Natalizumab had significant effects on all relapse endpoints examined; when compared to AVONEX® over two years, including a 55% reduction in the annualized relapse rate, with 54% of natalizumab-treated patients relapse-free compared to 32% of patients on AVONEX®. The MRI scans supported these clinically-observed effects. Also, natalizumab, when compared to AVONEX® therapy alone, improved the patients' quality of life, as measured by the physical components of the SF-36, with a trend on the mental component. All these effects were consistent and significant across subgroups defined by baseline demographics and disease activity.

Progressive Multifocal Leukoencephalopathy

PML is an infectious disease of the central nervous system caused by JCV infection of oligodendrocytes. JCV is a human polyoma virus that is believed to infect the majority of healthy individuals at an early age. The seroprevalence of anti-JCV antibodies in healthy individuals has been estimated to range from 20% to 80% depending upon the testing methodology (Knowles et al., *J. Med. Virol.* 71:115-123 (2003)); Knowles and Sasnauskas, *J. Virol. Methods.* 109: 47-54 (2003)).

PML occurs predominantly in immunocompromised individuals with an age-adjusted death rate due to PML of 3.3 per million persons (in 1994), 89% of whom were AIDS patients (Holman et al., *Neuroepidemiol.* 17:303-309 (1998)). However, rare PML cases have also been reported in patients with autoimmune disorders who received immunosuppressive therapy; among these, three patients with rheumatoid arthritis (Sponzilli et al., *Neurology* 25:664-668 (1975); Rankin et al., *J. Rheumatol* 22:777-79 (1995); Durez et al., *Arthritis Rheum.* 46 (9S):536 (2002)), one of whom was treated with tumor necrosis factor (TNF) antagonist (Durez et al., *Arthritis Rheum.* 46 (9S):536 (2002)). There was also a report of PML in a Crohn's Disease patient, but the concomitant treatments were not specified (Garrels et al., *Am. J. Neuroradiol.* 17:597-600 (1996)).

The pathology of PML is distinctive and comprises multiple foci of demyelination of varying size from pinpoint lesions to areas of several centimeters. The lesions may occur anywhere but are usually in the cerebral hemispheres, less often in the cerebellum and brain stem and rarely in the spinal cord. The oligodendrocytes in the peripheral zone surrounding an area of demyelination are grossly abnormal. The nuclei of abnormal oligodendrocytes are packed with JC virions. Typically, PML evolves gradually, with impairment of mental function and disturbance of speech and vision. Movement may also be affected. The disease then progresses rapidly and the patient is severely disabled, eventually becoming demented, blind, and paralyzed; coma and death follow.

The presence of JCV in the blood and urine of PML patients and healthy, immunocompetent individuals has been described (Kitamura et al., *J. Infect. Dis.* 161:1128-1133 (1990); Tornatore et al., *Ann. Neurol.* 31:454-462 (1992); Dorries et al., *Virology* 198:59-70 (1994); Sundsfjord et al., *J. Infect. Dis.* 169:485-490 (1994); Agostini et al., *J. Clin. Microbiol.* 34:159-164 (1996); Dubois et al., *AIDS* 10:353-358 (1996); Knowles et al., *J. Med. Virol.* 59:474-479 (1999); Dorries et al., *J. Neurovirol.* 9(Suppl 1):81-87 (2003)). These findings are neither predictive nor diagnostic of PML in these patients; thus the relationship of blood or urine viral load to PML is unclear.

The clinical presentation of PML is largely dependent upon the size and distribution of the white matter lesions that develop as a result of viral infection, demyelination, and glial cell lysis. However, clinical features of the presentation help differentiate it from the demyelination associated with MS. In contrast to MS, PML involvement of the spinal cord or optic nerves is rare. Instead, about one-third of patients will present with visual field loss or cortical blindness with another third presenting with altered mentation or behavior changes (Dworkin et al., *Curr. Clin. Top. Infect. Dis.* 22:181-195 (2002)). Also unlike MS, hemiparesis is a common presenting symptom. These symptoms are typically sub-acute in onset and follow a slowly progressive course. Often, patients and their families are the first to notice the onset of PML through changes in the ability to perform routine activities of daily living, even prior to presentation with changes on neurological examination.

MRI is a sensitive tool for the detection of PML lesions in the setting of clinical signs or symptoms, although it may lack specificity. Typical MS lesions, demyelination from other causes (e.g., encephalomyelitis, HIV encephalopathy), gliosis, and edema can often have an appearance similar to early PML lesions. However, as shown in Table 1, there are features of PML lesions that help differentiate them from other etiologies (Post et al., *Am. J. Neuroradiol.* 20:1896-1906 (1999); Yousry et al. *N. Engl. J. Med.* in press (2006); (Berger et al., *Ann. Neurol.* 44:341-349 (1998); Hoffmann et al., *J. Neurol. Neurosurg. Psychiatry* 74:1142-1144 (2003); Langer-Gould et al., *N. Engl. J. Med.* 353:375-381 (2005)).

TABLE 1

Differential Diagnosis of MS and PML

|  | MS | PML |
| --- | --- | --- |
| Location of new lesions | Mostly focal, may affect entire brain and spinal cord, in white and possibly gray matter; | Diffuse, mainly sub-cortical, rarely periventricular, almost exclusively in white matter, although occasional extension to gray matter seen; |
|  | Posterior fossa lesions rarely seen | Posterior fossa frequently involved (cerebellum) |
| Borders | Sharp edges, shapes mostly round or finger-like (especially periventricular), confluent with other single lesions, U-fibers may be involved | Ill-defined edges, infiltrating, irregular in shape, confined to white matter, sparing gray matter, pushing against cortex, U-fibers destroyed |
| Mode of extension | Focal, enlarging of lesions within days/weeks, later decreasing in size within months | Diffuse, asymmetrical, extending homogeneously, no confluence with other lesions, defined to white matter tracks, sparing cortex, continuous progression |
| Mass effect | Acute lesions may show some mass effect | No mass effect even in large lesions (but process is slightly pushing against cortex) |
| T2-weighted sequence | Acute lesions: hyperintense center, isointense ring, discrete hyperintensity outside ring structure; Sub-acute/chronic lesions: hyperintense, no ring structure | Diffuse hyperintense, slightly increased intensity of newly involved areas compared to old areas, little irregular signal intensity of lesions |
| T1-weighted sequence | Acute lesions: densely hypointense (large lesion) or isointense (small lesion), increasing signal intensity over time in 80%, decreasing signal intensity (axonal loss) in about 20% | Slightly hypointense from the onset, signal intensity decreasing over time and along the affected area, no reversion of signal intensity |
| Flair sequence | Hyperintense, sharply delineated | Hyperintensity more obvious, true extension of abnormality more clearly visible than in T2-weighted images |

TABLE 1-continued

Differential Diagnosis of MS and PML

| | MS | PML |
|---|---|---|
| Enhancement | Acute lesions: dense homogeneous enhancement, sharp edges<br>Sub-acute lesions: ring-enhancement<br>Chronic lesions: no enhancement | Usually no enhancement even in large lesions, in HIV+ patients some peripheral enhancement possible, especially under therapy |
| Atrophy | Focal atrophy possible due to focal white matter degeneration, no progression | No focal atrophy since extending pathological process is slightly pushing against cortex (extension of tissue) |

MRI analysis can provide a differential diagnosis of MS and PML in patients receiving natalizumab. Patients suspected of PML demonstrate the presence of multifocal, asymmetric, white-matter lesions reflective of demyelination by MRI. $T_2$-weighted and fluid-attenuated inversion recovery (FLAIR) MRI reveals hyperintense lesions throughout the supratentorial subcortical white matter (Post et al., *Am. J. Neuroradiol.* 20:1896-1906 (1999)). White matter lesions of PML are typically not surrounded by edema, do not produce a mass effect, and do not enhance in the presence of gadolinium contrast material (Post et al., *Am. J. Neuroradiol.* 20:1896-1906 (1999)). However, hyperintense $T_2$-weighted and FLAIR images are not specific for demyelination and may represent gliosis or edema. Other demyelinating, encephalopathic or ischemic processes such as MS, postviral encephalitis, HIV encephalopathy and infarction, may demonstrate similar non-specific imaging features (Olsen et al., *Radiology* 169:445-448 (1988), Hurley et al., *J. Neuropsychiatry Clin. Neurosci.* 15:1-6 (2003)). The location of lesions and their morphological characteristics, the absence or an atypical presence of gadolinium enhancement on $T_1$-weighted images, and the implementation of magnetization transfer MRI may also help differentiate the demyelination of PML from other demyelinating processes, edema or gliosis (Ernst et al., *Radiology* 210:439-543 (1999); Hurley et al., J. *Neuropsychiatry Clin. Neurosci.* 15:1-6 (2003)).

The clinical diagnosis of PML is confirmed by histological and virological examination of brain material obtained by brain biopsy or at postmortem. Before a biopsy is done, both serum and CSF should be examined for antibodies against JCV. A positive result will not confirm PML, but a negative result makes the diagnosis of PML very unlikely. It is rare to detect antibodies against JC in the CSF, and when they are detected, it is suggestive of active multiplication of JCV within the CNS. The brain biopsy or autopsy material can be examined by electron microscopy or immunohistologic electron microscopy. The specimen can also be examined directly for JCV antigen by immunofluorescence or immunoperoxidase staining. Viral isolation of JCV has been reported to be difficult, but may be attempted from primary human fetal glial cells. The presence of the virus in culture is confirmed by electron microscopy, immunofluorescence, or haemagglutination.

PCR analysis of the CSF for JC viral DNA is a highly sensitive and specific test for the diagnosis of PML. The specificity of this test approaches 100%, with a sensitivity ranging from 60% to 90% (Henson et al., *Neurology* 41:1967-1971 (1991); Gibson et al., *J. Med. Virol.* 39:278-281 (1993); Weber et al., *AIDS* 8:49-57 (1994a); Weber et al. *J. Infect. Dis.* 169:1138-1141 (1994b); Vago et al., *J. Acquir. Imm. Defic. Syndr. Hum. Retrovirol.* 12:139-146 (1996)). In cases with a high clinical suspicion of PML and negative CSF results, repeat testing often leads to detection of JC viral DNA. As such, PCR analysis of the CSF for JC viral DNA has grown to be the preferred method to confirm the diagnosis of PML.

Untreated, PML patients have a mortality rate of 30% to 50% during the first three months (Koralnik, *Curr. Opt. Neurol.* 17:365-370 (2004)). Prior to the introduction of highly active antiretroviral treatment (HAART) for HIV, about 10% of patients with PML survived for longer than one year. However, since the advent of HAART, about 50% of patients with PML survive for longer than one year due to restoration of immune function as CD4 counts increased as a result of immune reconstitution inflammatory syndrome (Geschwind et al., *J. Neurovirol.* 7:353-357 (2001); Berger et al., *Ann. Neurol.* 44:341-349 (1998); Clifford et al., *Neurology* 52:623-625 (1999); Tantisiriwat et al., *Clin. Infect. Dis.* 28:1152-1154 (1999)).

Currently, there is no established drug treatment for PML. Various medications have been tested, including acyclovir, idoxuridine, vidarabine, amantadine, adenine arabinoside, cytosine arabinoside (cytarabine), cidofovir, interferon α, interleukin-2 (IL-2), zidovudine, camptothecin, and topotecan (Koralnik, *Curr. Opt. Neurol.* 17:365-370 (2004); Dworkin et al., *Curr. Clin. Top. Infect. Dis.* 22:181-195 (2002); Seth et al., *J. Neurovirol.* 9:236-246 (2003); Collazos, *CNS Drugs* 17:869-887 (2003); Mamidi et al., *J. Neurovirol.* 8:158-167 (2002); Przepiorka et al., *Bone Marrow Transplant;* 20:983-987 (1997); Redington et al., *Arch. Neurol.* 59:712-718 (2002); Padgett et al., *Prog. Clin. Biol. Res.* 105:107-117 (1983)). However, the survival of patients with PML appears to be best correlated with immune reconstitution. In transplant patients with PML, early dosage reduction or/and discontinuation of immunosuppressive therapy was associated with favorable clinical outcome after PML diagnosis (Crowder et al., *Am. J. Transplant* 5:1151-1158 (2005); Shirit et al., *Transpl. Int.* 17:658-665 (2005)).

JC Virus (JCV)

JCV is a member of the class of human polyomavirus, which belong to the Papovaviridae family of small, nonenveloped viruses with a closed, circular double DNA-stranded genome. Polyomaviruses can be distinguished from papillomaviruses by virtue of their smaller virion size and different genomic size and organization. Polyomaviruses are ubiquitous in nature and can be isolated from a number of species. JCV was first isolated from the brain tissue of a patient with progressive multifocal leukoencephalopathy (PML). JCV shares 75% nucleotide sequence homology with the BK human polyomavirus (BKV), which was isolated from the urine of a renal transplant patient with postoperative ureteral stenosis. BKV and JCV each share 70% homology with SV40. The two are not serologically cross-reactive and serologic tests for antibodies are able to distinguish between BKV and JCV (Demeter, in Mandell et al., eds., Mandell, Douglas and Bennett's Principles and Practice of Infectious Diseases, 4th edition, Vol. 2. New York, N.Y.: Churchill Livingstone; 1995:1400-1406).

JCV infection is usually sub-clinical, is almost universal, occurs in childhood, and persists for life. It is estimated that 60-80% of adults in Europe and the United States have antibodies to JCV and that 50% of young adults in the age range of 30-39 years have been infected with JCV. JCV and BKV are believed to circulate independently. It has been proposed that JCV establishes latent infections in the kidney and/or the CNS after a primary infection (Demeter, in Mandell et al., eds., Mandell, Douglas and Bennett's Principles and Practice of Infectious Diseases, 4th edition, Vol. 2. New York, N.Y.: Churchill Livingstone; 1995:1400-1406). During immunosuppression, it has been postulated that latent JCV is reactivated in the kidney, which may lead to viruria. While viruria may have some predictive value for PML, since it does not occur in the majority of PML cases, measuring JCV in the urine alone is not sufficient to diagnose JCV.

When JCV travels through the bloodstream to the brain, it may attack myelin-producing cells. The resulting brain infection produces neurological symptoms which may include ataxia, loss of cognitive function, visual loss, changes in balance and coordination, and loss of sensation. Death commonly occurs within two years following diagnosis.

No specific antiviral therapy that has been proven effective for JCV, and current treatment of immunocompromised patients is primarily supportive and intended to reduce immunosuppression. Cidofovir is currently being studied as a treatment option for transplant patients, and cytarabine can be used in the treatment of PML, although there is currently conflicting data regarding the efficacy of the latter (Demeter, in Mandell et al., eds., Mandell, Douglas and Bennett's Principles and Practice of Infectious Diseases, 4th edition, Vol. 2. New York, N.Y.: Churchill Livingstone; 1995:1400-1406; Salmaggi, *Neurol. Sci.* 22:17-20 (2001)).

The cellular receptor for JCV has been reported to be the serotonin 5HT2(A) receptor (Elphick et al., *Science* 306: 1380-1383 (2004)). In vitro, the antipsychotic medications chlorpromazine and clozapine were shown to block the serotonin 5HT2(A) receptor and to block JCV cell entry. Unfortunately, however, chlorpromazine and clozapine have such significant side effects and toxicities, e.g., extrapyramidal symptoms and the possibility of bone marrow dyscrasias that they may be problematic to use clinically. The invention provides that newer atypical antipsychotics, such as zisprasidone, risperidone, and olanzapine—medicines with much better side effect and toxicity profiles than the older antipsychotics—are significantly more potent 5HT2 (A) receptor antagonists in vitro than chlorpromazine and clozapine.

A wide variety of serological tests are available to detect JCV, e.g., complement-fixation (CFT), haemagglutination-inhibition (HAI), enzyme-linked immunoassay (EIA), radioimmunoassay (RIA), particle agglutination, immunofluorescence (IF), single radial hemolysis, and Western blot. The sensitivity and specificity varies greatly between different techniques. Most techniques will detect all classes of antibody, whereas some assays e.g., RIA, EIA, and IF can be designed to detect one specific class, for example, IgM, IgG, or IgA.

Patient Selection Based on Safety and Efficacy

Appropriate patient selection helps maximize the benefit-risk profile of natalizumab. Natalizumab has demonstrated efficacy in treatment-naïve patients with mild to moderate disability (EDSS 0 to 5.0) with recent clinical disease activity (for example, one relapse in the year prior to study entry). It has also demonstrated efficacy in patients with mild to moderate disability with continuing disease activity despite treatment with β-interferon (for example, one relapse in the year prior to study entry, while receiving AVONEX®).

The benefit/risk ratio is altered in certain other patient populations. Patients without evidence of relapsing disease, that is, without evidence of inflammatory activity clinically or by MRI, such as those with relatively "benign" inactive disease, or chronic-progressive forms of MS, were excluded from the Phase 3 trials, thus, natalizumab has not been completely evaluated in these cohorts. The benefit-risk is also altered in patients with a single clinical event without features suggestive of MS.

Patients who are clinically stable on current therapy also have an altered benefit/risk ratio. If safety or tolerability concerns exist on the current treatment, or imaging studies indicate active inflammatory sub-clinical disease, natalizumab treatment would be appropriate. In considering the benefit-risk ratio, it should be considered whether the patient has previously suffered a hypersensitivity reaction or developed persistent antibodies to natalizumab. Re-dosing of natalizumab following a hypersensitivity reaction was not assessed in Phase 3 trials. Persistent antibodies against natalizumab lead to a loss of efficacy and an increase in infusion-related side effects. Patients who are immunocompromised from any cause, including use of immunosuppressant medications have an independent risk factor for PML and other opportunistic infections and should not receive natalizumab.

Another criteria for patient selection is a pre-infusion checklist used by the infusion nurse to facilitate early detection of PML and minimize inappropriate use of natalizumab. The checklist prompts the nurse to ask the patient about continuously worsening neurological symptoms that have persisted over several days, e.g., new or sudden decline in thinking, eyesight, balance, or strength. If a patient reports having any symptoms described by the checklist, the nurse is instructed not to administer natalizumab and to refer the patient to his or her physician.

This checklist also ascertains that the patient will be receiving natalizumab for the treatment of relapsing MS, has never been diagnosed with PML, and is not currently experiencing any continuously worsening symptoms that have persisted over several days. It further ascertains that the patient is not known to be suffering from HIV or a hematologic malignancy, nor has had an organ transplant. It confirms that the patient is not currently receiving treatment with an anti-neoplastic, immunomodulatory, or immunosuppressive agent and that the patient has read the natalizumab patient information leaflet, which is further described in Example 2.

Methods of Treatment

Pharmaceutical compositions of natalizumab will be administered intravenously. Pharmaceutical compositions of natalizumab are provided at a dose from approximately 1 to 5 mg antibody per kilogram of body weight. In an embodiment, a standard dose of 300 mg natalizumab diluted with 100 ml 0.9% sodium chloride is injected intravenously once every four weeks. The dose maybe repeated at intervals from two to eight weeks. For example, a treatment regimen may comprise 3 mg antibody per kilogram of body weight repeated at approximately a four week interval. Intermittent, e.g., monthly, intravenous administration may be viewed as desirable by patients deterred by daily, every-other-day, or weekly self-injection.

Informing Patients and Caregivers

In the US, patients with MS receive medical treatment by a relatively small group of physicians, primarily neurologists. Approximately 6,000 physicians treat 90% of patients with MS. This is in contrast to 170,000 family practitioners that treat primary care diseases in the US. A dedicated force of physicians and sales representatives can interact with neurologists and, other healthcare professionals who care for patients with MS. Consequently, nearly all physicians who will prescribe natalizumab can readily be contacted.

Because PML is a disease of the central nervous system, the targeted prescribers of natalizumab are also the best-qualified physicians to diagnose and manage PML. Neurologists have the expertise to monitor subjects for signs and symptoms indicative of PML and select appropriate diagnostic tests to diagnose a patient with PML.

Also, patients with MS are knowledgeable about their treatment options. They are generally a young and highly-motivated. In a recent survey, 94% to 99% of patients with MS were aware of their treatment options, including β-interferons and glatiramer acetate (Biogen Idec). During the period when natalizumab was available commercially, 79% of patients with MS were aware of the introduction of natalizumab treatment. Also, feedback from patients with MS indicated that the risk of PML with natalizumab has been broadly disseminated in the MS community. Thus, the targeted patient population is likely to want to learn more about the risks of PML with natalizumab.

Accordingly, the invention provides for informing the prescribing physician and the patient about the mental and physical symptoms of progressive multifocal leukoencephalopathy and instructing the patient to report to the physician in the presence of at least one symptom. These informational efforts will provide relapsing MS patients and their physicians with the information they need to make informed benefit-risk decisions about the use of this highly effective therapy, while actively managing recognized risks. The invention also provides informational tools for patients and physicians to promote informed benefit-risk decisions, to ensure appropriate use of natalizumab, and to reinforce the importance of early detection of PML through clinical vigilance. For example, the invention provides protocols for informing physicians and patients of the risks of natalizumab treatment and for actively assessing and managing these risks on an ongoing basis. These protocols are based upon current medical and scientific knowledge of PML and information gained from the safety evaluation of natalizumab-treated patients.

This information provides a setting wherein appropriate patients receive natalizumab. Accordingly, the invention provides that patients and physicians receive significant information regarding the risks associated with natalizumab so that informed benefit-risk decisions can be made regarding initiation of natalizumab treatment.

The invention also provides that the prescription for natalizumab serves as an enrollment form for physicians and for patients that collects information regarding risk factors for PML, and requires an acknowledgement by physicians and patients that they understand the risks associated with natalizumab treatment.

Infusion sites undergo a mandatory authorization process that must be completed prior to shipment of natalizumab to that site. A controlled, centralized, distribution system ships natalizumab only to authorized infusion sites, allowing for directed delivery of informational tools and timely receipt of new safety information. The shipping destination and the number of all vials are tracked through the distribution system. Through the controlled distribution system, all physicians and patients who use natalizumab at initiation of treatment PML are enrolled in a surveillance program that continues informing about and assessing the risk of PML. For example, large registry studies continually assess the safety of natalizumab in the commercial setting.

The surveillance program monitors patients receiving natalizumab treatment by routinely assessing them for PML, using the opportunity afforded through the periodic interactions between the heath care providers and patients at the time of infusion. In an embodiment, these periodic interactions occur approximately once a month. Patients with possible PML are thus rapidly identified, so that natalizumab can be immediately discontinued and the proper assessments completed. This information, surveillance, and monitoring program provides timely information regarding safety issues related to natalizumab.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims. Moreover, advantages described in the body of the specification, if not included in the claims, are not per se limitations to the claimed invention.

It is to be understood that both the foregoing general description and the following detailed description are exemplary and explanatory only and are not restrictive of the invention, as claimed. Moreover, it must be understood that the invention is not limited to the particular embodiments described, as such may, of course, vary. Further, the terminology used to describe particular embodiments is not intended to be limiting, since the scope of the present invention will be limited only by its claims. The claims do not encompass embodiments in the public domain.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. The specification is most thoroughly understood in light of the references cited herein.

It must be noted that, as used herein and in the appended claims, the singular forms "a," "or," and "the" include plural referents unless the context clearly dictates otherwise. Thus, for example, reference to "a subject polypeptide" includes a plurality of such polypeptides and reference to "the agent" includes reference to one or more agents and equivalents thereof known to those skilled in the art, and so forth.

Further, all numbers expressing quantities of ingredients, reaction conditions, % purity, polypeptide and polynucleotide lengths, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed.

Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Efficacy of Natalizumab

The efficacy of natalizumab over a two year period has been demonstrated in two Phase 3 trials (Polman et al., N. Engl. J. Med. in press (2006); Rudick et al. N. Engl. J. Med. in press (2006)). In one study, natalizumab was given as monotherapy to treatment-naïve MS patients and its efficacy was compared to placebo. In the other study, natalizumab was given to patients who were experiencing relapses despite concurrent AVONEX® therapy and its efficacy was compared to that of AVONEX (interferon β-1a) plus placebo. Data through two years have confirmed the benefit that led to accelerated approval at one year. These data show that natalizumab is highly efficacious in delaying the time to onset of sustained progression of disability, in reducing annualized relapse rate, in attenuating MRI lesions, and in improving the quality of life of patients compared both to placebo and the active AVONEX® control group.

Both Phase 3 studies had similar designs. In the monotherapy study, 942 untreated relapsing remitting MS patients were randomized to receive natalizumab or placebo for 120 weeks (30 infusions) using a 2:1 allocation. In the add-on study, 1,171 patients who had been receiving weekly intramuscular injections of 30 μg AVONEX®, but who had relapsed despite this treatment, were randomized using a 1:1 allocation to add natalizumab or placebo to their regimen, also for 120 weeks.

Efficacy parameters included EDSS scores, MS relapses, brain MRI scans, MSFC scores, visual function tests, and quality of life. EDSS and MSFC were measured every 12 weeks, brain MRI scans and quality of life questionnaires at baseline and every year, and MS relapses on an ongoing basis.

Treatment with natalizumab as monotherapy in treatment-naïve patients had profound effects on the time to onset of sustained progression in disability and on annualized relapse rate, the two primary endpoints, as shown in Table 2. These significant effects were confirmed versus AVONEX® alone.

TABLE 2

Efficacy of Natalizumab in Phase 3 Studies

| | Monotherapy | | Add-on therapy | |
| --- | --- | --- | --- | --- |
| | Placebo | 300 mg natalizumab | AVONEX + placebo | AVONEX + 300 mg natalizumab |
| Number of patients | 315 | 627 | 582 | 589 |
| Percentage of patients with sustained progression of disability | 29% | 17% | 29% | 23% |
| Hazard ratio (95% confidence interval) | | 0.58 (0.43, 0.77) | | 0.76 (0.61, 0.96) |
| Risk reduction | | 42% | | 24% |
| p-value | | p < 0.001 | | p = 0.024 |
| Annualized relapse rate | 0.733 | 0.235 | 0.749 | 0.336 |
| Relative reduction | | 68% | | 55% |
| p-value | | p < 0.001 | | p < 0.001 |

The patient population in the two Phase 3 studies were relapsing MS patients according to the criteria of the International Panel on the Diagnosis of Multiple Sclerosis (McDonald et al., Ann. Neurol. 50:121-127 (2001)). It encompassed a broad range of ages and disease severity, and represented the current relapsing MS population with active disease, consistent with the approved indication. Patients with primary- or secondary-progressive MS were excluded.

The patient populations targeted for the two studies differed. Patients in the monotherapy study were essentially naïve to treatment with an immunomodulatory drug for MS. Specifically, patients may not have had treatment with any immunomodulator (β-interferon or glatiramer acetate) for a period longer than six months and not within six months of the beginning of the study. The result was a young, mostly female, MS population with a moderate degree of baseline disease activity (typical of the general MS population), very few of whom had tried another immunomodulator prior to study entry.

Patients in the add-on therapy study were required to have received AVONEX® for the previous year and to have had a relapse during that time while on AVONEX® treatment. This resulted in a population somewhat older than that in the monotherapy study, with a longer disease duration. However, patients in the add-on therapy study had a similar degree of disease activity as those in the monotherapy study, despite AVONEX® treatment.

Example 2

Caregiver and Patient Information

Prior to starting natalizumab treatment, the physician will provide the patient with the Patient Information Leaflet, will ask the patient to read it, and will discuss the information with the patient. The Patient Information Leaflet is intended to provide information to patients with MS on the risks of natalizumab treatment, including the risk of PML. In addition, the leaflet instructs patients to promptly report any continuously worsening neurological symptoms to their physician, thereby reinforcing the importance of early detection of PML. The Patient Information Leaflet will be widely disseminated. In addition to distribution to prescribers and infusion centers, the leaflet will be available on the internet and distributed to patient groups such as the National Multiple Sclerosis Society (NMSS).

Once the decision to use natalizumab is made, the physician and patient will complete the enrollment form. The enrollment form includes a natalizumab prescription and a Patient-Physician Acknowledgement. The physician and patient will sign the Patient-Physician Acknowledgment to document that they discussed and understood natalizumab benefits and risks, including the risk of PML, and that the physician is prescribing natalizumab for the treatment of relapsing MS.

By signing the Patient-Physician Acknowledgement, the physician also acknowledges that he or she has read the full prescribing information for natalizumab, is aware that natalizumab is associated with an increased risk of PML, which causes death or disability, has discussed the risks and benefits of natalizumab with his or her patient, and is prescribing natalizumab for the treatment of relapsing MS. The physician also acknowledges that the patient is not immunocompromised, and has instructed the patient to promptly report to his or her physician any continuously worsening symptoms that persist over several days.

By signing the Patient-Physician Acknowledgement, the patient acknowledges that he or she has read the Patient Information Leaflet, is aware that natalizumab is associated with an increased risk of PML, which causes death and disability, has discussed the risks and benefits of natalizumab with his or her physician, and understands that it is important to promptly report to his or her physician any continuously worsening symptoms lasting over several days. The patient and physician information are entered into a central database, thus initiating enrollment into the natalizumab risk management program.

Each enrolled patient is assigned a case manager who can answer questions about natalizumab, provide insurance coverage research, and match the patient to an appropriate infusion center. These services will be provided again upon natalizumab re-introduction and are another reason for patients and physicians to use the enrollment form. In addition, informational materials for natalizumab will inform physicians of the need to use the enrollment form for all natalizumab-treated patients and Biogen Idec and Elan sales representatives will be trained to reinforce the importance of using the form with all neurologists. Finally, neurologists and MS patients have provided feedback on the natalizumab risk management program and strongly support the use of the enrollment form. With the re-introduction of natalizumab, procedures described herein will be monitored.

The invention claimed is:

1. A method of treating a patient with an inflammatory or autoimmune disease comprising the steps of:
    (a) testing the patient for the presence of anti-JC virus (JCV) antibodies by a method consisting of measuring the presence of anti-JCV antibodies in the serum or plasma of a blood sample from the patient;
    (b) initiating treatment of the patient tested in step (a) by administering natalizumab to the patient in the event the sample is negative for anti-JCV antibodies;
    (c) testing the patient treated in step (b) for indicators of progressive multifocal leukoencephalopathy (PML) by detecting the presence of JCV in the patient's cerebrospinal fluid, or detecting clinical and/or radiologic symptoms of PML in said patient, and
    (d) further administering natalizumab to the patient in the absence of indicators of PML or discontinuing natalizumab treatment in the presence of indicators of PML.

2. The method of claim 1, wherein the indicators of PML comprise new or worsening neurological symptoms.

3. The method of claim 2, wherein the neurological symptoms comprise one or more of central blindness, mental confusion, personality change, and dyskinesia.

4. The method of claim 1, wherein the radiologic symptoms comprise lesions detected by a Gd-enhanced magnetic resonance imaging scan.

5. The method of claim 1, wherein the disease is multiple sclerosis.

6. The method of claim 5, wherein the multiple sclerosis is selected from relapsing remitting, secondary progressive, primary progressive, and chronic progressive multiple sclerosis.

7. The method of claim 6, wherein the multiple sclerosis (MS) is relapsing remitting MS.

8. The method of claim 6, wherein the multiple sclerosis is secondary progressive MS.

9. The method of claim 6, wherein the multiple sclerosis is primary progressive MS.

10. The method of claim 6, wherein the multiple sclerosis is chronic progressive multiple sclerosis.

11. The method of claim 1, wherein the disease is inflammatory bowel disease.

12. The method of claim 11, wherein the inflammatory bowel disease is Crohn's disease.

* * * * *